US010542868B2

(12) United States Patent
Gordon et al.

(10) Patent No.: US 10,542,868 B2
(45) Date of Patent: Jan. 28, 2020

(54) DEVICES, SYSTEMS, AND METHODS USING MATING CATHETER TIPS AND TOOLS

(71) Applicant: INTUITIVE SURGICAL OPERATIONS, INC., Sunnyvale, CA (US)

(72) Inventors: Lucas S. Gordon, Mountain View, CA (US); Randall L. Schlesinger, San Mateo, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 418 days.

(21) Appl. No.: 15/508,923

(22) PCT Filed: Sep. 3, 2015

(86) PCT No.: PCT/US2015/048383
§ 371 (c)(1),
(2) Date: Mar. 5, 2017

(87) PCT Pub. No.: WO2016/040128
PCT Pub. Date: Mar. 17, 2016

(65) Prior Publication Data
US 2017/0296038 A1 Oct. 19, 2017

Related U.S. Application Data
(60) Provisional application No. 62/048,504, filed on Sep. 10, 2014.

(51) Int. Cl.
A61B 1/12 (2006.01)
A61B 1/015 (2006.01)
(Continued)

(52) U.S. Cl.
CPC .......... *A61B 1/00105* (2013.01); *A61B 1/005* (2013.01); *A61B 1/00091* (2013.01);
(Continued)

(58) Field of Classification Search
CPC ............ A61B 1/00091; A61B 1/00105; A61B 1/00135; A61B 1/00137; A61B 1/00163; A61B 1/015; A61B 1/126; A61B 1/127
See application file for complete search history.

(56) References Cited

U.S. PATENT DOCUMENTS 5,339,800 A * 8/1994 Wiita ................. A61B 1/00091
600/109
5,575,756 A * 11/1996 Karasawa .......... A61B 1/00068
600/121

(Continued)

FOREIGN PATENT DOCUMENTS

CN 103813744 A 5/2014
CN 107072521 A 8/2017
(Continued)

OTHER PUBLICATIONS

Office Action dated Jun. 26, 2018 for Chinese Application No. 201580058846.3 filed Sep. 3, 2015, 16 pages.
(Continued)

*Primary Examiner* — John P Leubecker
(74) *Attorney, Agent, or Firm* — Haynes and Boone, LLP

(57) ABSTRACT

A medical instrument system comprises an imaging probe including a distal tip terminating at a first distal end of the imaging probe and a lens disposed at the first distal end. The imaging probe including a first sealing feature on an external surface of the imaging probe. The medical instrument also comprises an elongated medical instrument including a distal portion terminating at a second distal end and including a working channel configured to slidably receive the
(Continued)

imaging probe. The working channel including a second sealing feature on a surface of the working channel. The first sealing feature and the second sealing feature are shaped and configured to contact one another to prevent the passage of fluid between the first and second sealing features.

24 Claims, 11 Drawing Sheets

(51) Int. Cl.
  *A61B 1/00* (2006.01)
  *A61B 1/005* (2006.01)
  *A61B 1/018* (2006.01)
  *A61B 1/05* (2006.01)
(52) U.S. Cl.
  CPC .......... *A61B 1/00163* (2013.01); *A61B 1/015* (2013.01); *A61B 1/018* (2013.01); *A61B 1/05* (2013.01); *A61B 1/126* (2013.01)

(56) References Cited

U.S. PATENT DOCUMENTS

| | | | | |
|---|---|---|---|---|
| 5,637,075 | A * | 6/1997 | Kikawada | A61B 1/00142 600/105 |
| 5,697,888 | A * | 12/1997 | Kobayashi | A61B 1/00068 137/606 |
| 5,989,183 | A * | 11/1999 | Reisdorf | A61B 1/00091 600/121 |
| 6,110,103 | A | 8/2000 | Donofrio | |
| 7,316,681 | B2 | 1/2008 | Madhani et al. | |
| 9,259,274 | B2 | 2/2016 | Prisco | |
| 9,452,276 | B2 | 9/2016 | Duindam et al. | |
| 2006/0020165 | A1 * | 1/2006 | Adams | A61B 1/00094 600/121 |
| 2007/0038213 | A1 * | 2/2007 | Machiya | A61B 18/1492 606/45 |
| 2007/0123971 | A1 | 5/2007 | Kennedy et al. | |
| 2008/0188715 | A1 | 8/2008 | Fujimoto | |
| 2009/0105739 | A1 * | 4/2009 | Toyonaga | A61B 18/1492 606/169 |
| 2009/0259103 | A1 | 10/2009 | Hirata | |
| 2013/0204085 | A1 * | 8/2013 | Alexander | A61B 1/05 600/109 |
| 2013/0331730 | A1 * | 12/2013 | Fenech | A61B 1/126 600/560 |
| 2014/0094659 | A1 | 4/2014 | Hamazaki et al. | |
| 2014/0207134 | A1 * | 7/2014 | Wake | A61B 18/14 606/39 |
| 2016/0220301 | A1 * | 8/2016 | Yamamoto | A61B 18/12 |
| 2017/0238795 | A1 | 8/2017 | Blumenkranz et al. | |

FOREIGN PATENT DOCUMENTS

| | | |
|---|---|---|
| JP | H07222712 A | 8/1995 |
| JP | H07313442 A | 12/1995 |
| JP | 2001353161 A | 12/2001 |
| JP | 2009247566 A | 10/2009 |
| JP | 2012005533 A | 1/2012 |
| JP | 2012045325 A | 3/2012 |
| JP | 2013162863 A | 8/2013 |
| WO | WO-2016025465 A1 | 2/2016 |

OTHER PUBLICATIONS

Co-pending U.S. Appl. No. 62/037,299, filed Aug. 14, 2014.
International Search Report and Written Opinion for Application No. PCT/US15/48383, dated Dec. 16, 2015, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP15840494.7, dated May 23, 2018, 7 pages.
International Preliminary Report on Patentability for Application No. PCT/US2015/048383, dated Mar. 23, 2017, 10 pages.

* cited by examiner

DEVICES, SYSTEMS, AND METHODS USING MATING CATHETER TIPS AND TOOLS

RELATED APPLICATIONS

This application is the U.S. national phase of International Application No. PCT/US2015/048383, filed Sep. 3, 2015, which designated the U.S. and claims priority to provisional patent application 62/048,504, filed on Sep. 10, 2014, the contents of each of which are incorporated by herein by reference.

FIELD

The present disclosure is directed to devices, systems, and methods for cleaning a medical instrument, and more particularly to devices, systems, and methods for controlling fluid flow into or out of a medical instrument during a minimally invasive procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Minimally invasive medical procedures may rely upon visualization systems to find a target location and perform various operations. Particularly, a visualization system may help a minimally invasive medical instrument navigate natural or surgically created passageways in anatomical systems to reach the target tissue location. For example, the visualization system may help guide the minimally invasive medical instrument through natural passageways in the lungs, the colon, the intestines, the kidneys, the heart, the circulatory system, or the like. Some minimally invasive medical instruments may be teleoperated or otherwise computer-assisted. In some instances, the visualization system comprises and imaging tool received within an instrument channel or lumen.

During navigation of the medical instrument, or during an operation performed by the medical instrument, the lens of the visualization system may become obstructed or clouded by patient tissue or fluids. Such obstructions can make navigation or operation more difficult, and various methods have been developed to assist the surgeon in clearing the obstructions off the lens. Some types of medical devices include cleaning systems that utilize a cleaning lumen extending from a proximal end to a distal end of the instrument that terminates in a nozzle extending past the distal end of the instrument. The nozzle is configured to deliver cleaning fluid across the lens. In other instances, the surgeon may gently brush the distal end of the instrument across the patient's tissue to wipe off accumulated liquids. However, it can be difficult to keep liquid from pooling between the instrument channel and the tool (e.g., the imaging tool), which enables the pooled liquid to wick back onto the lens. In addition, it can be difficult to effectively and efficiently clean the cleaning lumen and nozzle after completion of the medical procedure.

Thus, it is desirable to provide medical devices, systems, and methods that enable effective and efficient cleaning of visualization systems associated with medical instruments during and after minimally invasive medical procedures. The devices, systems, and methods disclosed herein overcome one or more of the deficiencies of the prior art.

SUMMARY

The embodiments of the invention are summarized by the claims that follow below.

In one embodiment, a medical instrument system comprises an imaging probe including a distal tip terminating at a first distal end of the imaging probe and a lens disposed at the first distal end. The imaging probe includes a first sealing feature on an external surface of the imaging probe. The medical instrument also comprises an elongated medical instrument including a distal portion terminating at a second distal end and including a working channel configured to slidably receive the imaging probe. The working channel includes a second sealing feature on a surface of the working channel. The first sealing feature and the second sealing feature are shaped and configured to contact one another to prevent the passage of fluid between the first and second sealing features.

In another embodiment, a medical instrument system comprises an imaging probe including a distal tip terminating at a first distal end of the imaging probe. The distal tip includes a first sealing feature and a fluid direction surface. The system also comprises an elongated medical instrument having a distal portion terminating at a second distal end. The elongated medical instrument including a working channel and a second sealing feature on a surface of the working channel. The first sealing feature and the second sealing feature are shaped and configured to contact one another to prevent the passage of fluid between the first and second sealing features. The first and second sealing features are in contact, a gap is formed between the fluid direction surface and the second distal end of the medical instrument to direct passage of fluid from the working channel across the distal tip of the imaging probe.

In another embodiment, a method comprises positioning an imaging probe within a working channel of an elongate medical instrument. The imaging probe includes a distal tip having a first shape and the working channel includes a distal portion having a second shape. The first shape and the second shapes are complementary. The method also includes selectively sealing a fluid passage between the imaging probe and the medical instrument by advancing the distal tip of the imaging probe within the distal portion of the medical instrument.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
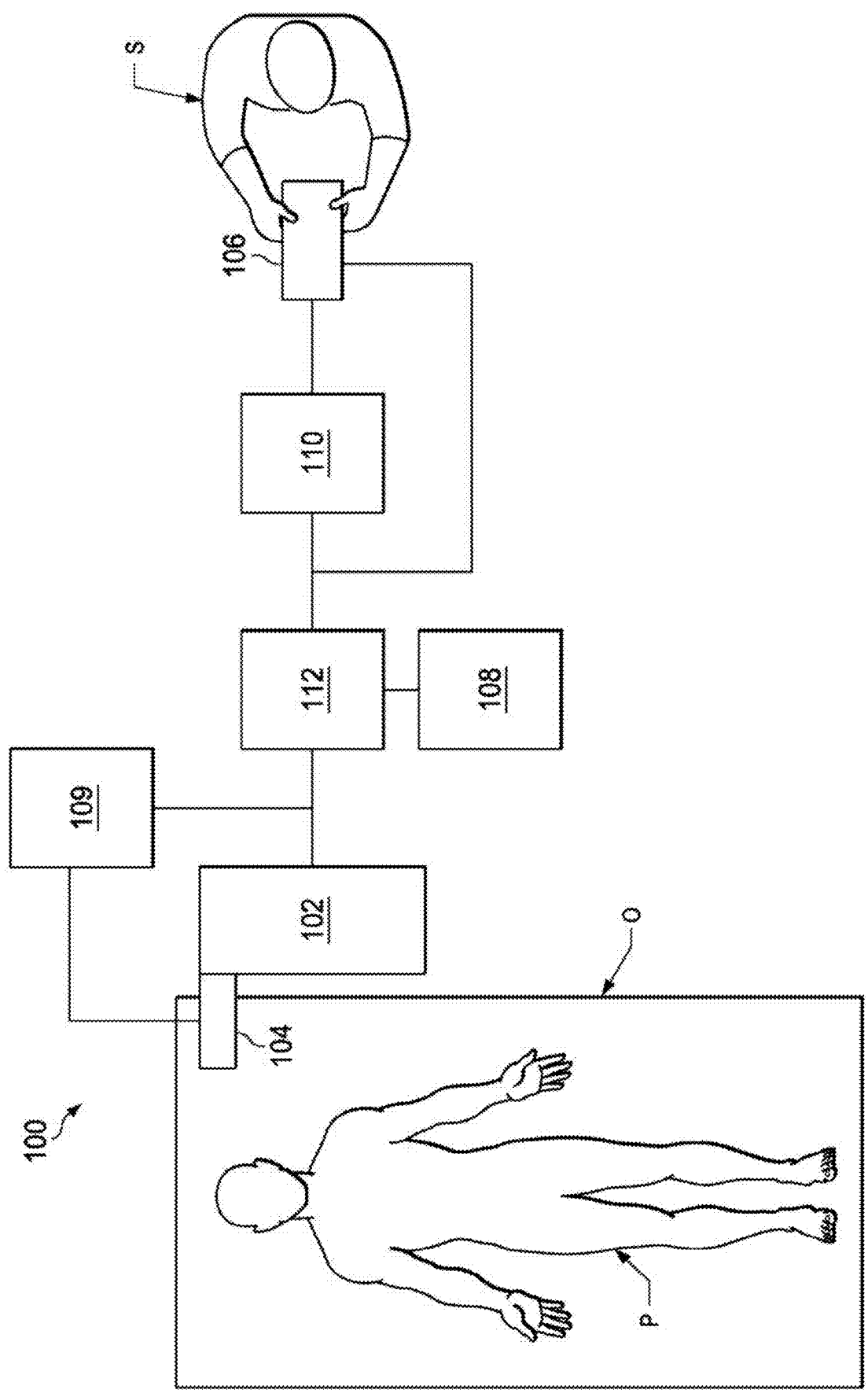
FIG. 1 is a diagram showing an illustrative teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, surgical instruments are used in many orientations and positions, and there terms are not intended to be limiting and absolute.

The present disclosure relates generally to using devices and systems that provide mating surfaces between a working channel tip within a hollow medical instrument and a tool tip to enhance the performance and maintenance of teleoperational medical systems and/or instruments used in a variety of medical procedures, including without limitation diagnostic, surgical, and/or therapeutic procedures. Several different embodiments of mating instrument channels and tool tips are described. The tools may comprise any of a variety of tools, including, without limitation, imaging devices and biopsy instruments. In some embodiments, the mating tips are configured to partially or completely seal together to prevent fluid from pooling between the working channel and the tool. In some embodiments, the mating tips are configured to provide a gap between the medical instrument and the tool that allows the passage of cleaning fluid to the distal tip of the tool. Such embodiments may enhance the ease and efficiency of cleaning the system after use by eliminating the need to use an instrument having a conventional flushing lumen, which may include a small internal diameter and be difficult to clean. In some embodiments, the mating surfaces are similarly angled or tapered to provide the seal preventing fluid from pooling between the working channel and the tool without allowing for the passage of cleaning fluid between the medical instrument and the tool. Some embodiments include features configured to repel the liquid from the surface of an imaging tool such as, by way of non-limiting example, a raised lens surface or a hydrophobic lens coating. In some embodiments, the mating surfaces include a keying feature to enhance the interlocking between the medical instrument and the tool and to minimize rotation of the tool tip relative to the tip of the medical instrument. In some embodiments, the tapered instrument tip provides a mating surface for a biopsy sheath and needle, and the mating surface may function to increase biopsy accuracy by preventing the needle from deflecting from an intended trajectory toward the target tissue when inserting the needle through tissue.

Those of skill in the art will realize that the devices, systems, and methods described herein may be utilized in similar (e.g., non-teleoperational) applications benefiting from more effective and efficient cleaning of visualization systems during and after medical procedures. By utilizing the devices, systems, and methods described herein, a user may experience more effective and more efficient interaction with the imaging instruments and/or visualization systems of a medical system.

According to various embodiments, medical procedures, such as biopsy procedures, may be performed using a teleoperational system to guide instrument delivery. Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument system 104. The operator input system 106 may be referred to as a master or surgeon's console.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. More specifically, in response to the surgeon's input commands, the control system 112 effects servomechanical movement of medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., control system 112). The motors include drive systems which when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes an image capture system 108 with one or more sub-systems for capturing images from the surgical workspace at the distal end of the medical instrument system 104. The system operator sees images, captured by an image capture system 108, presented for viewing on a display system 110 operatively coupled to or incorporated into the operator input system 106. The display system 110 displays an image or representation of the surgical site and medical instrument system(s) 104 as generated by sub-systems of the image capture system 108. The display system 110 and the operator input system 106 may be oriented so the operator can control the medical instrument system 104 and the operator input system 106 with the perception of telepresence. The display system 110 may include multiple displays such as separate right and left displays for presenting separate images to each eye of the operator, thus allowing the operator to view stereo images.

In some embodiments, as shown in FIG. 1, the teleoperational medical system 100 also includes a fluid management system 109 for delivering or evacuating fluid through the medical instrument system 104. For example, the fluid management system 109 may include a fluid delivery system for delivering air, carbon dioxide, or saline through the instrument to clean the distal end of the instrument. The fluid management system 109 may also include a suction system to remove fluid and debris from the patient workspace. In other embodiments, the teleoperational medical system 100 lacks the fluid management system 109. In various embodiments, the fluid management system is used to maintain a low positive pressure between the catheter and the instrument sufficient to prevent or minimize movement of fluid from the patient anatomy into the working channel. This low positive pressure may be applied such that little or no fluid from the fluid management system is delivered into the patient anatomy.

Alternatively or additionally, the display system 110 may present images of the surgical site (and/or anatomical site) recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented pre-operative or intra-operative images may include two-dimensional, three-dimensional, or four-dimensional (including e.g., time based or velocity based information) images and associated image data sets for reproducing the images.

The teleoperational medical system 100 also includes a control system 112. The control system 112 includes at least one memory and at least one processor (not shown), and typically a plurality of processors, for effecting control between the medical instrument system 104, the operator input system 106, the image capture system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, the control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system (s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
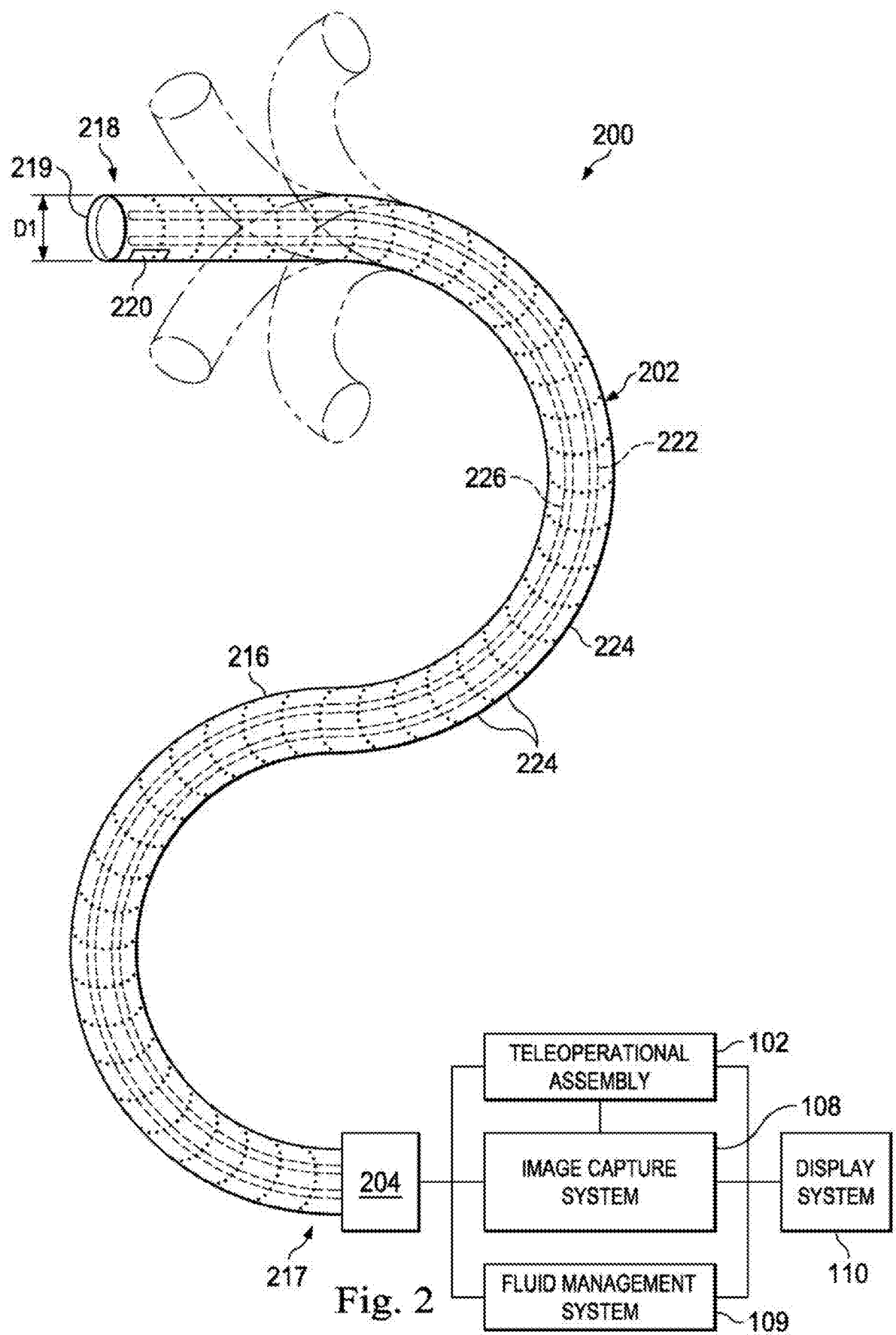
FIG. 2 is a diagram showing an illustrative medical instrument system comprising an endoscopic visualization system according to one embodiment of the present disclosure.

FIG. 2 illustrates a medical instrument system 200, which may be used as the medical instrument system 104 of teleoperational medical system 100 for insertion into a patient's body at either a natural orifice or a surgically created orifice. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. The flexible body 216 has a working channel 219 with a diameter D1. The working channel or tool channel 219 may be sized to receive an instrument or tool and/or to direct fluid through the flexible body. In one embodiment, the flexible body 216 has an approximately 3 mm outer diameter. Other flexible body outer diameters may be larger or smaller. In one embodiment, the flexible body 216 has an approximately 2 mm inner diameter (i.e., the working channel 219 has an inner diameter D1 of approximately 2 mm). Other tool channel inner diameters may be larger or smaller. The entire length of the body 216, between the distal end 218 and the proximal end 217, may be effectively divided into the segments 224.

The medical instrument system may optionally include a position sensor system 220. The position sensor system 220 may be a component of an EM sensor system with the sensor 220 including one or more conductive coils that may be subjected to an externally generated electromagnetic field.

The catheter system 202 may optionally include a shape sensor 222 for determining the position, orientation, speed, velocity, pose, and/or shape of the catheter tip at distal end 218 and/or of one or more segments 224 along the body 216. The shape sensor 222 may include an optical fiber aligned with the flexible catheter body 216 (e.g., provided within an interior channel (not shown) or mounted externally). In one embodiment, the optical fiber has a diameter of approximately 200 In other embodiments, the dimensions may be larger or smaller. The optical fiber of the shape sensor system 222 forms a fiber optic bend sensor for determining the shape of the catheter system 202.

The flexible catheter body 216 includes one or more working channels sized and shaped to receive an auxiliary instrument 226 (not shown). For example, in some embodiments, the auxiliary instrument 226 may be received within the working channel 219. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like.

In various embodiments, the auxiliary tool 226 may be an image capture probe (e.g., an imaging probe 300 described below with reference to FIG. 3B), such as an endoscope, that includes a distal portion with a stereoscopic or monoscopic camera at or near the distal end 218 of the flexible catheter body 216 for capturing images (including video images) that are processed by the image capture system 108 for display. The image capture probe may include a cable coupled to the camera for transmitting the captured image data. Alternatively, the image capture instrument may be a fiber-optic bundle, such as a fiberscope, that couples to the image capture system 108. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like. In various embodiments, the medical instrument may include a rigid cannula (e.g. a rigid endoscope) rather than a flexible catheter.

In the embodiment of FIG. 2, the medical instrument system 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

To operate properly, the distal end of the catheter system 202 or other catheter instruments, bronchoscopes, or endoscopes should ideally remain free of obstructions or be frequently cleared of obstructions during use. The accumulation of patient fluids (e.g., mucous or blood), tissue, or cautery smoke on a lens of an imaging probe or at the opening of the working channel 219 may prevent the safe and time efficient nature of procedures using such instruments. Some cleaning methods involve injecting a fluid (e.g., gas or saline) through a dedicated cleaning lumen into nozzle aimed at the lens, swiping the distal end 218 of the catheter system 202 against patient tissue to remove debris, or removing the instrument (e.g., the auxiliary instrument 226 and/or the catheter body 216) from the patient and physically wiping the distal end free of debris. All of these procedures present various disadvantages, including the loss of time and ineffective clearing of debris, which can affect both patient safety and cost effectiveness. As mentioned above, it can be difficult to keep patient fluids, cleaning fluids, or the like from entering between the instrument channel and the tool (e.g., the imaging tool) when using the swiping method. The fluids may then pool within the instrument channel and later wick back onto the lens. In addition, it can be difficult to effectively and efficiently clean the cleaning lumen and nozzle after completion of the medical procedure. Moreover, the use of an injected fluid emerging from a nozzle extending past the distal end of the instrument to clean the distal end may be inadvisable in situations in which the instrument is inserted into a patient lumen (e.g., an airway passage of the lungs) and the outside diameter of the instrument tip completely or substantially fills the inside diameter of the patient lumen, sealing off the anatomical region distal of the instrument tip. Fluid injected to clean the instrument tip may cause the sealed off portion of the anatomical region to overinflate and rupture the surrounding tissue. For example, if the instrument is a bronchoscope in use in a lung, the region of the lung isolated by the impacted instrument may experience a rupturing of the lung wall or pleura, resulting in pneumothorax. According to devices, systems, and methods described herein, a mating configuration between the catheter body 216 and the auxiliary instrument 226 allows for more effective and efficient use and cleaning of the catheter system 202.

Figure 3A:
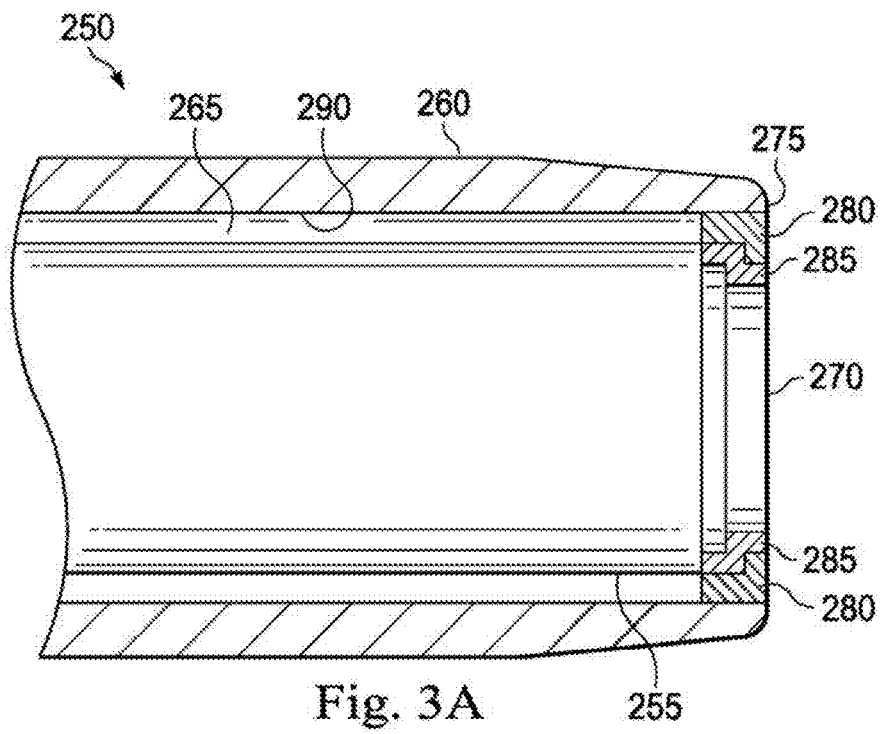
FIG. 3A is a side, cross-sectional view of the distal portion of an exemplary medical instrument system including an exemplary tool positioned within an exemplary medical instrument according to one embodiment of the present disclosure.

FIG. 3A is a side, cross-sectional view of an exemplary medical instrument system 250 including an exemplary tool 255 positioned within an exemplary medical instrument 260 according to one embodiment of the present disclosure. The medical instrument 260 may be the same as the catheter system 202 shown in FIG. 2. In the pictured embodiment, the medical instrument 260 is shown as an elongated tube. In other embodiments, the medical instrument 260 may comprise any of a variety of medical instruments, including, without limitation, an endoscope, a bronchoscope, a flexible catheter, and a rigid delivery instrument. According to the present example shown in FIG. 3A, the medical instrument 260 comprises a working channel 265 through which the tool 255 extends.

In the pictured embodiment, a distal end 270 of the tool 255 is substantially co-planar with a distal end 275 of the medical instrument 260 when the tool 255 is advanced fully within the medical instrument 260. In other embodiments, the distal end 270 of the tool 255 may be positioned slightly proximal to or slightly distal to the distal end 275 of the medical instrument 260 when the tool 255 is advanced fully within the medical instrument 260.

The medical instrument system 250 includes sealing features 280, 285 shaped and configured to selectively seal the space between the distal ends 270, 275 of the tool 255 and the medical instrument 260, respectively. As shown in FIG. 3A, the tool 255 is shaped and configured to be slidably received within the working channel 265 of the medical instrument 260. In the pictured embodiment, the working channel 265 includes the sealing feature 280, and the tool includes the sealing feature 285. The sealing features 280, 285 are shaped as complementary elements that mate together to prevent or minimize the passage of fluid from the distal ends 270, 275 into the working channel 265. In the pictured embodiment, the sealing features 280, 285 are shaped as lips, chamfered surfaces, or bevels. In other embodiments, the sealing features 280, 285 may comprise any of a variety of elements shaped and configured to interact or mate to selectively seal the space or gap between the distal ends 270, 275 of the tool 255 and the medical instrument 260, respectively. In some embodiments, the sealing features 280, 285 comprise mating three-dimensional protrusions and indentations, textured surfaces, or tapered surfaces.

The sealing feature 285 of the tool 255 is shaped to complement or mate with at least a portion of the sealing feature 580 of the instrument 260. In that regard, the sealing features 280, 285 may extend circumferentially 360 degrees around an inner surface 290 of the working channel 265 and the tool 255, respectively. In other embodiments, the sealing features 280, 285 may extend less than 360 degrees circumferentially around an inner surface 290 of the working channel 265 and the tool 255, respectively, thereby permitting the passage of fluid in an area where the sealing features do not mate. In some instances, when the tool 255 is fully advanced through the working channel 265, the sealing features 280 and 285 mate or contact one another to prevent fluid from pooling between the tool 255 and the working channel 265 (e.g., preventing the backflow of fluid, including both fluid emerging from the working channel 265 and fluid originating from the patient when, by way of non-limiting example, the user wipes the distal end 275 of the instrument 260 against patient tissue).

In some embodiments, the sealing features 280, 285 also act as interlocking features that cooperate or mate to align and position the tool 255 in the center of the working channel 265 and/or flush with the distal end 275 of the instrument 260. In some embodiments, the sealing features 280, 285 include additional interlocking features such as projections or indentations that cooperate or mate to align and position the tool 255 in the center of the working channel 265 and flush with the distal end 275 of the instrument 260. Other embodiments may include any of a variety of sealing features 280, 285 that are shaped and configured to contact one another to at least partially prevent fluid from passing between the working channel 265 and the tool 255 (e.g., in the area of contact).

Figure 3B:
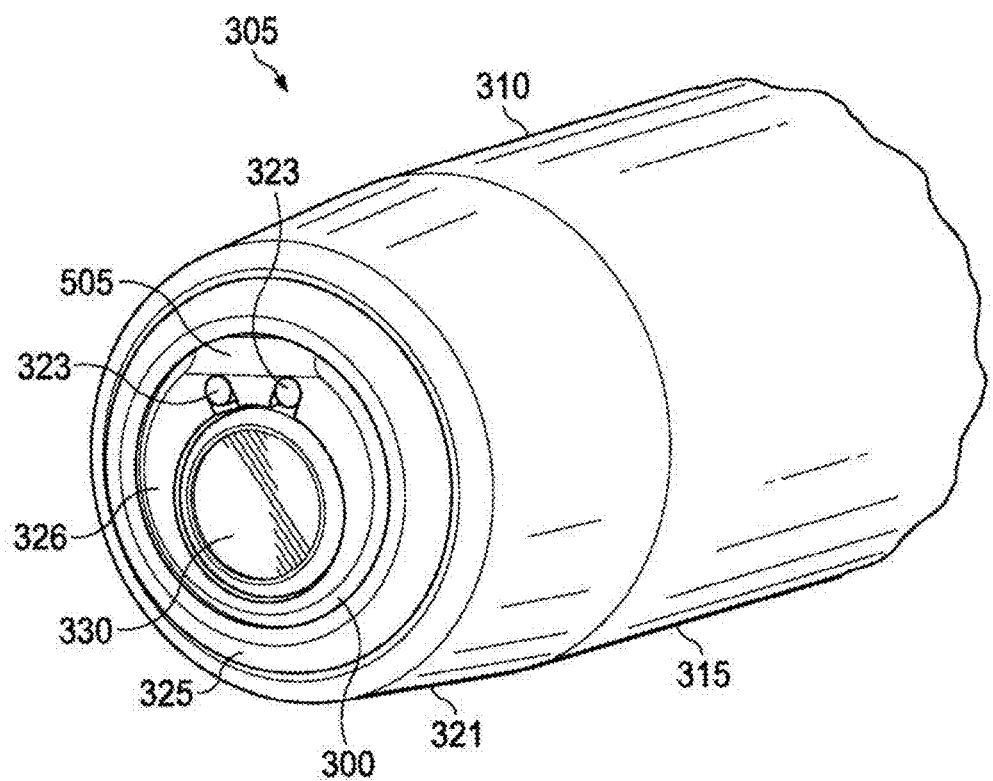
FIG. 3B is a perspective view of the distal portion of an exemplary medical instrument system including an exemplary imaging probe positioned within an exemplary catheter according to one embodiment of the present disclosure.
Figure 4:
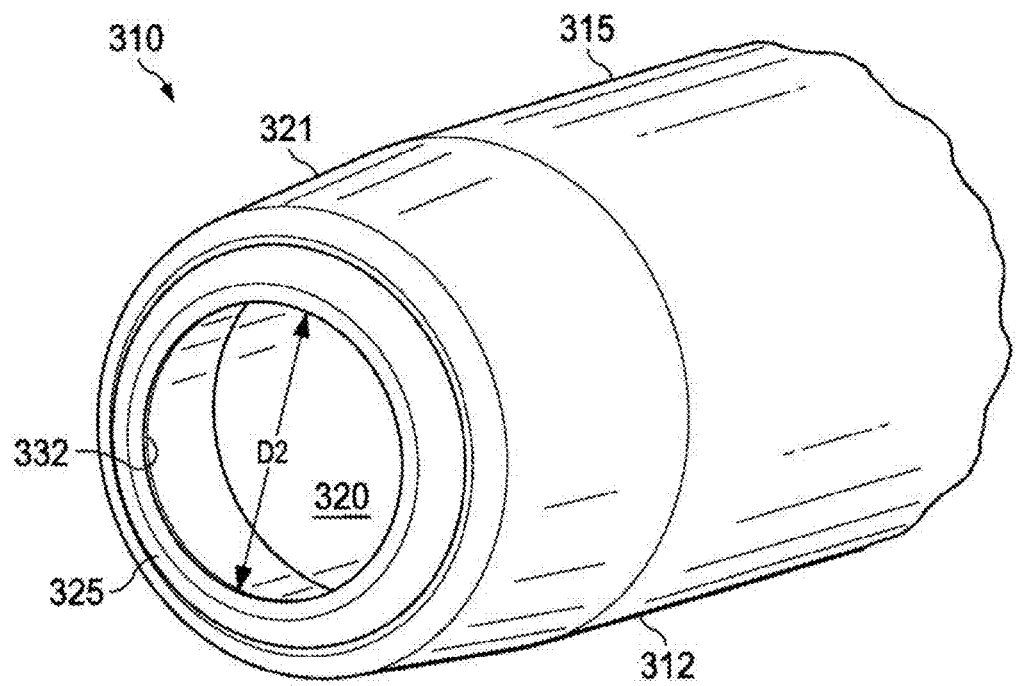
FIG. 4 is a perspective view of the distal portion of the exemplary catheter shown in FIG. 3B according to one embodiment of the present disclosure.
Figure 5:
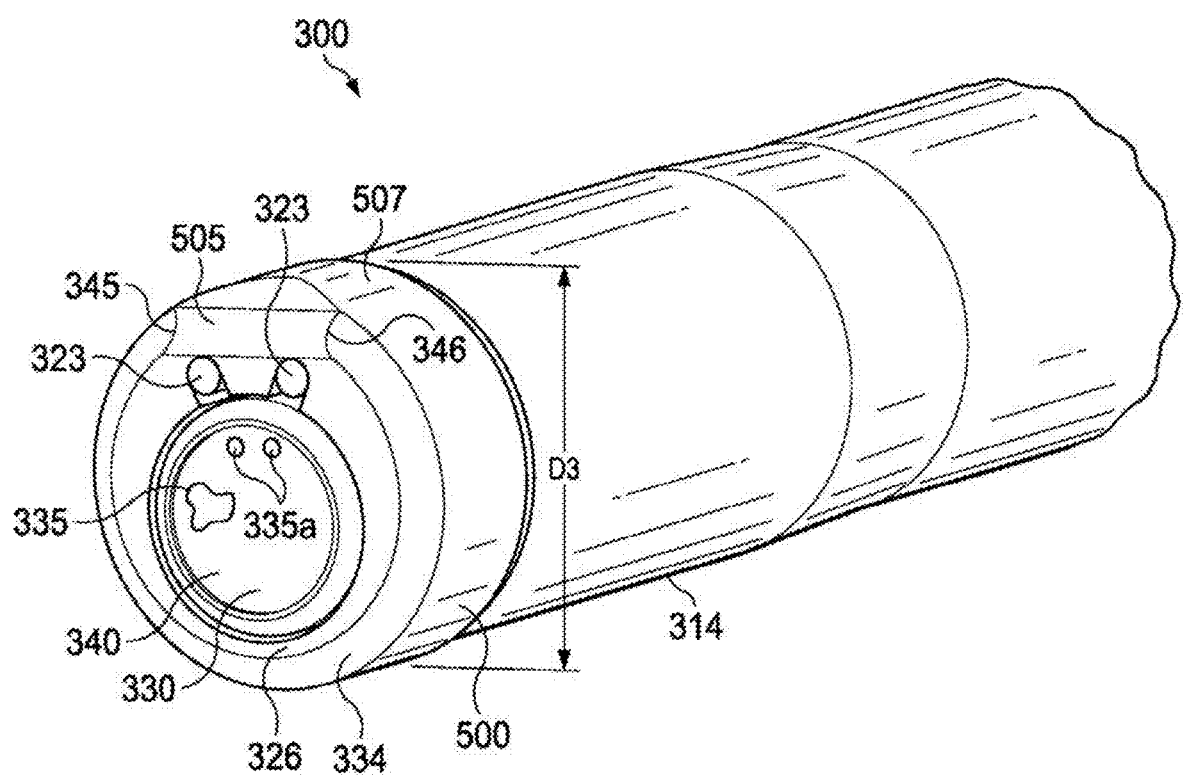
FIG. 5 is a perspective view of the distal portion of the exemplary imaging probe shown in FIG. 3B according to one embodiment of the present disclosure.

FIG. 3B is a perspective view of an exemplary medical instrument system 305 including the exemplary imaging probe 300 positioned within an exemplary medical instrument 310 according to one embodiment of the present disclosure. FIG. 4 is a perspective view of a distal portion 312 of the medical instrument 310 shown in FIG. 3B according to one embodiment of the present disclosure. FIG. 5 is a perspective view of a distal portion 314 of the imaging probe 300 shown in FIG. 3B according to one embodiment of the present disclosure.

The medical instrument 310 may be the same as the catheter system 202 shown in FIG. 2. In the pictured embodiment, the medical instrument 310 is shown as a flexible, elongated catheter. In other embodiments, the medical instrument 310 may comprise any of a variety of elongated medical instruments, including, without limitation, an endoscope, a bronchoscope, a flexible catheter, and a rigid delivery instrument. According to the present example shown in FIGS. 3B and 4, the medical instrument 310 comprises a catheter body 315 including a working channel 320 through which the elongated imaging probe 300 extends. In the pictured embodiment, the working channel 320 comprises a hollow, tubular space formed within the catheter body 315 of the instrument 310. The working channel 320 includes a distal inner diameter D2. In one embodiment, the distal inner diameter D2 measures approximately 2 mm. Other distal inner diameters D2 may be larger or smaller. In the pictured embodiment, the medical instrument 310 includes a tapered distal section 321 that terminates at the distal end 325 of the catheter body 315. In other embodiments, the distal section 321 is not tapered. In some embodiments, the distal section 321 is formed of radiopaque material, which may assist the user to visualize and guide the navigation of the distal section 321 of the catheter body 315 as the medical instrument 310 is moved through the patient's body. In some embodiments, the tapered distal section 321 is formed of a metal.

In the pictured embodiment, the imaging probe 300 includes two separate illumination elements 323. The illumination elements 323 may comprise illumination fibers configured to illuminate the patient tissue past a distal end 326 of the imaging probe 300 (e.g., that is being imaged by the imaging probe 300). Although the pictured embodiment includes 2 illumination elements 323, other embodiments may include any number of illumination elements or may lack illumination elements altogether.

The imaging probe 300 includes an imaging surface or lens 330. In various embodiments, the lens 330 may comprise a substantially flat imaging surface or a curved imaging surface. In various embodiments, the lens 330 may be substantially co-planar with the distal end 326 of the imaging probe 300 or slightly raised from the distal end 326 of the imaging probe 300. For example, in some embodiments, the lens 330 can protrude distally past the remainder of the distal end 326 of the imaging probe 300.

Figure 6:
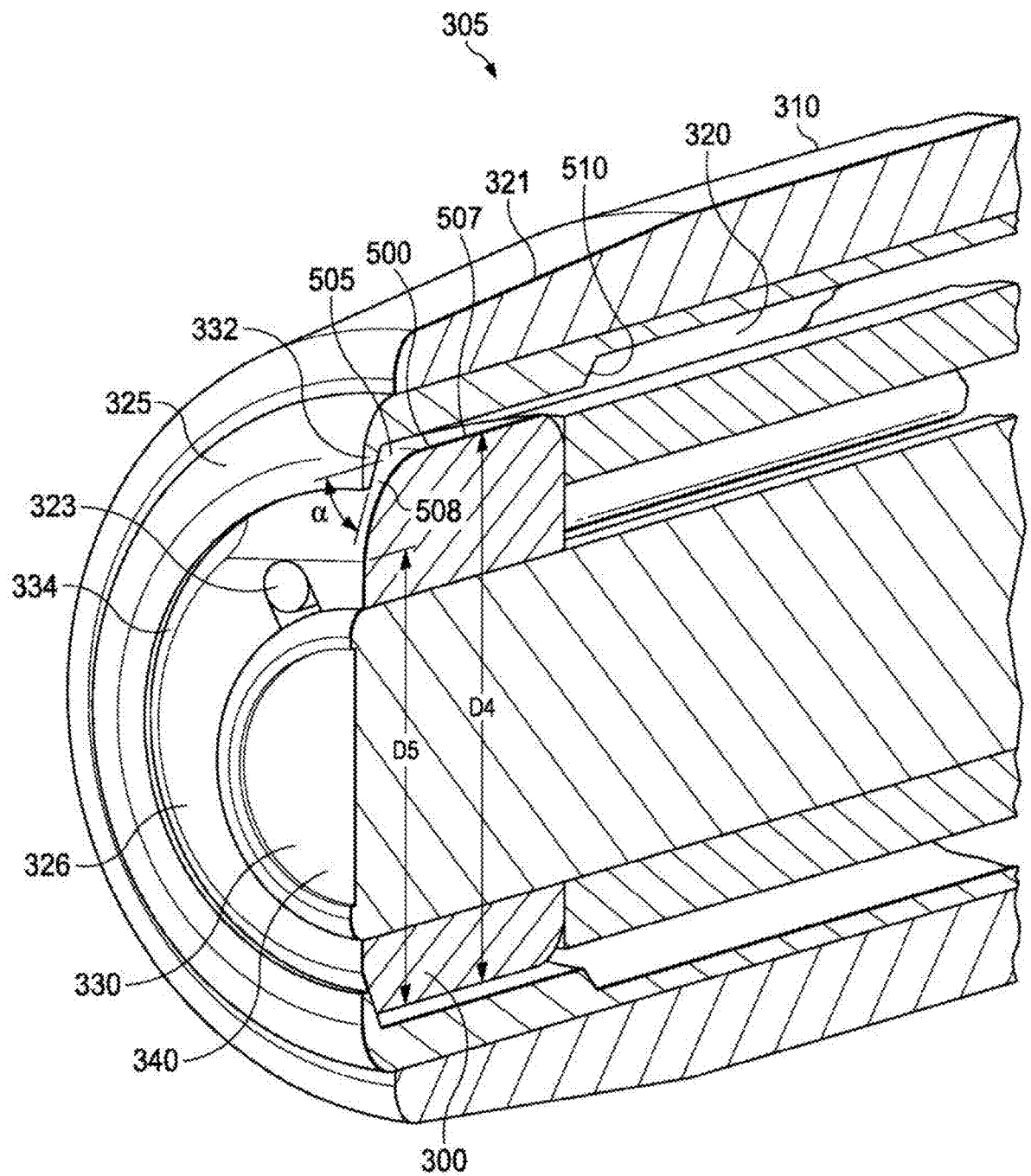
FIG. 6 is a perspective, cutaway view of the medical instrument system shown in FIG. 3B according to one embodiment of the present disclosure.

In some embodiments, the medical instrument system 305 includes a sealing feature shaped and configured to selectively seal the space between the distal ends of the imaging probe 300 and the medical instrument 310. As shown in FIGS. 3B and 5, the imaging probe 300 is shaped and configured to be slidably received within the working channel 320 of the medical instrument 310. As shown in FIGS. 4 and 6, in the pictured embodiment, the working channel 320 includes a sealing feature 332 shaped as an internal lip, chamfer, or bevel at the distal end 325 of the catheter body 315. The sealing feature 332 extends circumferentially 360 degrees around the inner surface 510 of the catheter body 315. As shown in FIGS. 5 and 6, the distal end 326 of the imaging probe 300 includes a matching or complementary sealing feature 334 shaped as an external bevel. The bevel 334 may extend circumferentially 360° around the distal end 326 or, as shown in FIG. 5, may extend circumferentially less than 360° between circumferential ends 345 and 346. The sealing feature 334 of the imaging probe 300 is shaped to complement or mate with at least a portion of the sealing feature 332 of the catheter body 315. In some instances, when the imaging probe 300 is fully advanced through the working channel 320, the sealing features 332 and 334 mate or contact one another to prevent fluid from pooling between the imaging probe 300 and the working channel 320 (e.g., preventing the backflow of fluid, including both fluid emerging from the working channel 320 and fluid originating from the patient, from the region of the lens 330 into the distal section 321 of the catheter body 315 when, by way of non-limiting example, the user wipes the distal end 325 of the catheter body against patient tissue). Additionally, a low positive pressure may be applied to the working channel between the catheter and the imaging probe to further prevent the inflow of fluid originating from the patient anatomy.

In some embodiments, the sealing features 332 and 334 also act as interlocking features that cooperate or mate to align and position the imaging probe 300 in the center of the working channel 320 and flush with the distal end 325 of the catheter body 315. In some embodiments, the sealing features 332 and 334 include additional interlocking features such as projections or indentations that cooperate or mate to align and position the imaging probe 300 in the center of the working channel 320 and flush with the distal end 325 of the catheter body 315. Other embodiments may include any of a variety of sealing features 332, 334 that are shaped and configured to contact one another to at least partially prevent fluid from passing between the working channel 320 and the imaging probe 300 (e.g., in the area of contact). Some embodiments may lack an internal and external bevel. For example, some embodiments may include sealing features comprising similarly tapered, complementary surfaces shaped and configured to contact one another along a portion of the working channel and the imaging probe (e.g., a tapered internal surface of the working channel and a tapered external surface of the imaging probe). Such embodiments are discussed in further detail below with reference to FIGS. 12-15.

In the pictured embodiment, the distal inner diameter D2 of the working channel 320 is sized to halt the distal progression of the distal end 326 of the imaging probe 300 past the distal end 325 of the catheter body 315. Thus, the distal end 326 of the imaging probe 300 does not extend beyond the distal end 325 of the catheter body 315. This configuration allows the user to wipe off accumulated fluid and other debris by, for example, wiping the end of the medical instrument 310 against the patient's tissues without unduly damaging patient tissues or accumulating pooled fluid between the imaging probe 300 and the working channel 320.

In other embodiments, a portion of the lens 330 of the imaging probe 300 may extend past the distal end 325 of the catheter body 315. Such a configuration may attract greater flow of cleaning fluid across the lens 330 as it emerges from the working channel 320, as described in more detail below with reference to FIG. 6.

As shown in FIG. 5, the lens 330 may have an obstruction 335 thereon. The obstruction 335 may include a cloudy substance or an object that obstructs vision through the visualization system. For example, patient tissue or patient fluids, such as blood or mucus, may stick to the surface of the lens 330 and cloud the surface of the lens 330. The obstruction 335 on the lens 330 may be visible in images received by the imaging probe 300 and displayed to the user.

In some cases, as shown in FIG. 5, the surface of the lens 330 may be coated with a hydrophobic coating 340. A hydrophobic coating reduces the degree to which liquid substances adhere to the surface of the lens 330. A liquid substance (e.g., the obstruction 335) on the hydrophobic lens coating or surface 340 may be more likely to form round beads 335a, which creates more surface area for the drag force. Specifically, fluid being projected parallel to the surface 340 will catch more of the beaded obstruction and more effectively move or dislodge the obstructions 335, 335a. Thus, removing obstructions from the surface of the lens 330 may be made more efficient by applying a hydrophobic coating 340 to the surface of the lens 330.

FIG. 6 is a perspective, cutaway view of the medical instrument system 305 shown in FIG. 3B, showing the imaging probe 300 positioned within the working channel 320 of the catheter body 315. As best shown in FIG. 6, the medical instrument system 305 provides a means of cleaning the imaging probe 300 by allowing a stream of cleaning fluid to flow from the working channel 320 across the lens 330 of the imaging probe 300. In particular, as shown in FIGS. 4-6, the imaging probe 300 includes a distal tip 500 having a sloped nozzle portion 505. The sloped nozzle portion extends between circumferential ends 345, 346. The distal tip 500 may be formed of metal or another substantially firm material, such as glass, a clear plastic, or an opaque plastic. Instead of having a uniformly circular profile and a uniform outer diameter D3 (FIG. 5) at the distal tip 500, the distal tip 500 has a notched or indented profile and the outer diameter D3 decreases at the sloped nozzle portion 505. As shown in FIG. 6, the outer diameter D3 of the distal tip 500 decreases gradually from an outer diameter D4 proximal to the sloped nozzle portion 505 to an outer diameter D5 distal to the sloped nozzle portion 505.

The sloped nozzle portion is angled downwards by an angle α. In the pictured embodiment, the angle α measures approximately 60°. In other embodiments, the angle α may be greater or smaller than 60°. The shape or contour of the nozzle portion 505 and the angle α may be optimized to minimize the destruction of fluid flow across the nozzle portion 505 and to maintain the flow as close as possible to an outer surface 507 (e.g., the distal end 326 and the lens 330) of the imaging probe 300. In the depicted embodiment the nozzle portion 505 has a curved slope, but in alternative embodiments may have a flat or textured slope. To increase the coanda effect between a fluid and the surface of the nozzle portion, the surface of the nozzle portion may be textured (e.g., dimpled or corrugated) to attract the fluid flow across the surface and the lens.

The pictured configuration enables cleaning fluid to flow from the working channel 320 over the sloped nozzle portion 505 and across the lens 330 to clear the lens 330 of any debris (e.g., the obstruction 335 shown in FIG. 5). In some embodiments, the angle α may be configured to direct fluid from the space 508 to flow parallel to the surface of the lens 330. The fluid may be, by way of non-limiting example, saline, carbon dioxide, or air. Fluid may be delivered through a space 508 formed between the sloped nozzle portion 505 and the inner surface 510 of the catheter body 315. The space 508 (i.e., the gap between the outer surface 507 of the sloped nozzle portion 505 and the working channel 320) provides a duct for delivering the cleaning fluid to the lens 330. In some instances, the space 508 measures 0.002 inches between the sloped nozzle portion 505 and the sealing feature 332 of the working channel 320. This measurement is provided for exemplary purposes only, and other dimensions are contemplated. The sealing features (or bevels) 332 and 334 act to prevent fluid from exiting the working channel 320 through areas other than the space 508 formed by the sloped nozzle portion 505. In some embodiments, the fluid management system 109 shown in FIG. 2 may provide short bursts of high-pressure fluid through the space 508 to clean the lens 330, as described in Prov. U.S. Pat. App. No. 62/037,299 which is incorporated by reference herein. In addition to the short pulse of high pressure fluid, a low pressure fluid stream may be used to prevent ingression of fluid from the patient anatomy into the working channel. The pressure may be constant and sufficiently low to keep patient fluid out, without significantly burdening the internal anatomic lumen or passageway of the patient. The high pressure, short pulse would be added to the constant low pressure.

Figure 7:
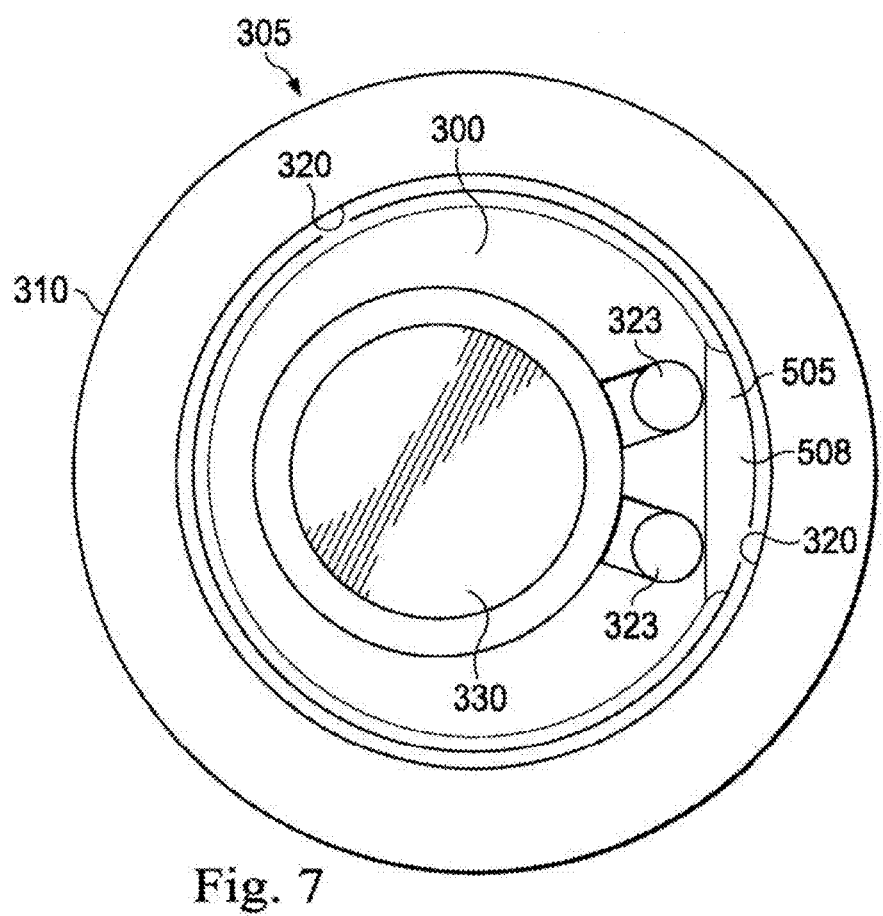
FIG. 7 is a front view of the medical instrument system shown in FIG. 3B according to one embodiment of the present disclosure.

FIG. 7 illustrates a front view of the medical instrument system 305, showing the imaging probe 300 positioned within the working channel 320 of the catheter body 315. FIG. 7 more clearly illustrates the space 508 formed between the sloped nozzle portion 505 and an inner surface 510 of the catheter body 315.

Figure 8:
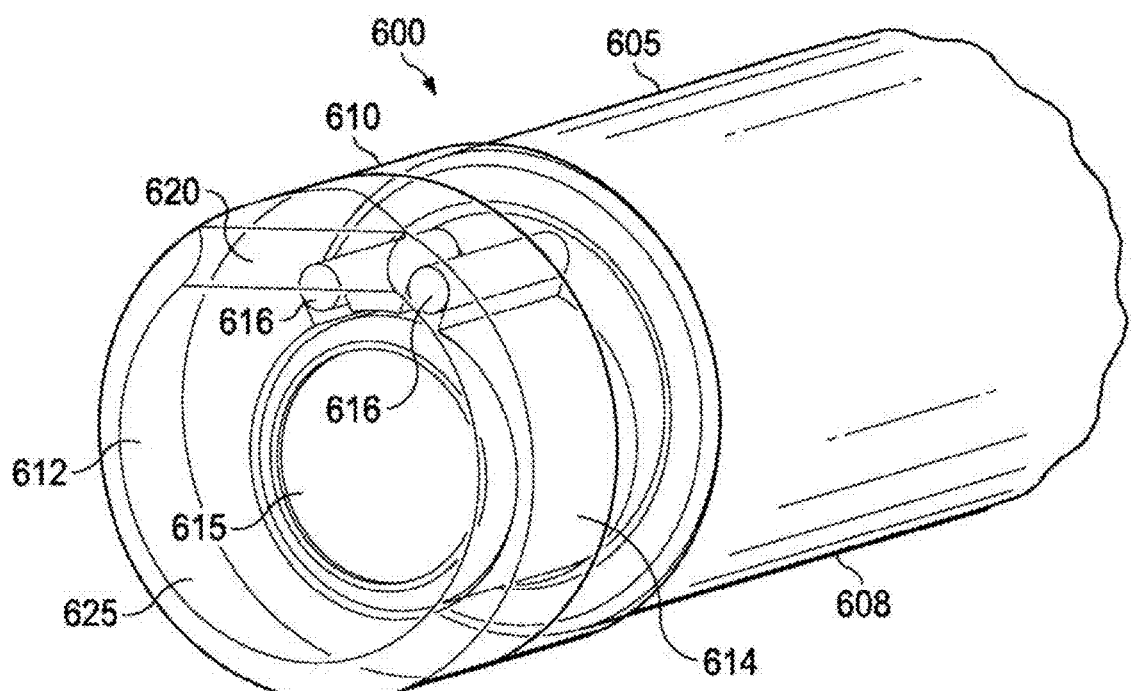
FIG. 8 is a perspective view of an exemplary imaging probe according to one embodiment of the present disclosure.
Figure 9:
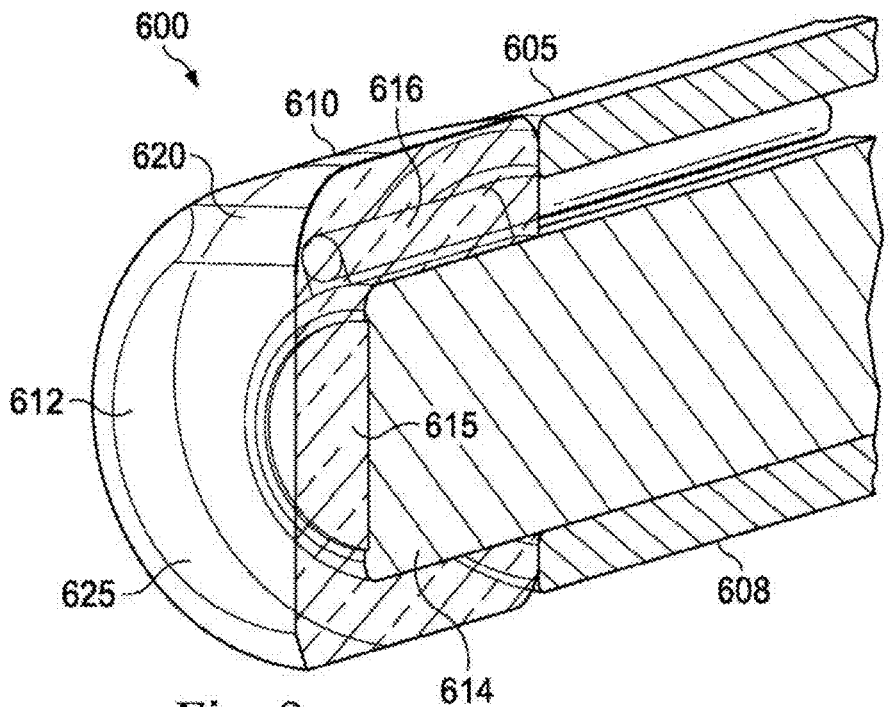
FIG. 9 is a perspective cutaway view of the imaging probe shown in FIG. 8 according to one embodiment of the present disclosure.

In some embodiments, the imaging probe includes a clear distal tip, as shown in FIGS. 8 and 9. FIG. 8 illustrates a perspective view of an exemplary imaging probe 600 according to one embodiment of the present disclosure. FIG. 9 illustrates a perspective, cutaway view of the imaging probe 600 according to one embodiment of the present disclosure. The imaging probe 600 is substantially similar to the imaging probe 300 shown in FIGS. 3B-7 except for the differences described herein. In particular, FIG. 8 illustrates a distal portion 605 of the imaging probe 600 including a shaft portion 608 and a clear distal tip 610 that terminates at a distal end 612. The clear distal tip 610 provides a clear viewing "window" that entirely surrounds and protects a lens 615 (and illumination fibers 616) of the imaging probe 600 while allowing a clear visualization path (and illumination path) for the imaging probe 600. The clear distal tip 610 provides a substantially smooth surface, which may reduce the accumulation of debris and improve the rinsing of debris from the tip 610. The clear distal tip 610 may be formed of any of a variety of optically clear materials, including, without limitation, glass and plastic. In some embodiments, the clear distal tip 610 is bonded directly to a camera or imaging device 614 of the imaging probe 600. As shown in FIG. 8, the clear distal tip 610 includes a sloped nozzle portion 620 that is substantially similar to the sloped nozzle portion 505 shown in FIGS. 5 and 6. When the imaging probe 600 is used in combination with a medical instrument such as the medical instrument 310, the cleaning fluid may be delivered through a space (not shown) formed between the sloped nozzle portion 620 of the clear distal tip 610 and an inner surface of the medical instrument (e.g., the inner surface 510 of the catheter body 315). In contrast to the embodiment shown in FIG. 6, the imaging probe 600 is configured to direct the cleaning fluid over a distal surface 625 of the clear distal tip 610 instead of the surface of the lens 615 itself.

Figure 10:
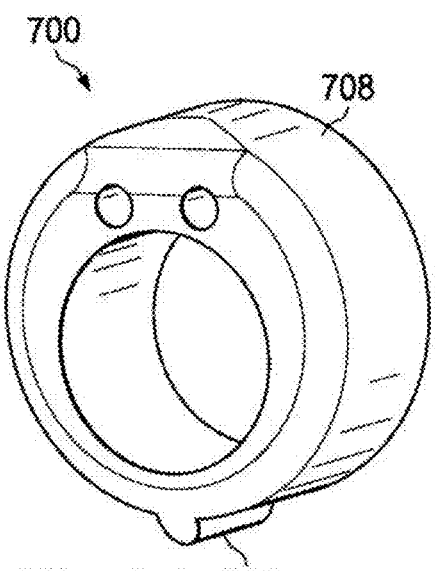
FIG. 10 is a perspective view of an exemplary distal tip of an imaging probe including an exemplary interlocking feature according to one embodiment of the present disclosure.
Figure 11:
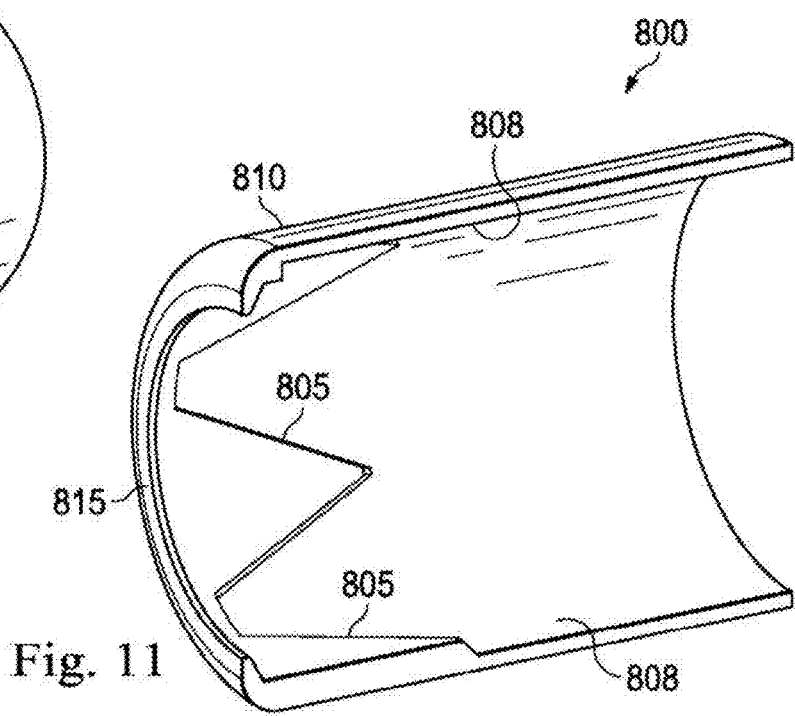
FIG. 11 is a perspective, cutaway view of an exemplary catheter body including an exemplary interlocking feature according to one embodiment of the present disclosure.

In some embodiments, as mentioned above, the medical instrument system 305 includes corresponding interlocking features disposed on each of the imaging probe 300 and the medical instrument 310 shaped and configured to selectively mate or releasably interlock the imaging probe 300 and the medical instrument 310. For example, as mentioned above in relation to FIG. 3B, in some embodiments, the sealing features 332, 334 can act as interlocking features as well as sealing features. In some instances, a first interlocking feature is disposed on the medical instrument 310, a second interlocking feature is disposed on the imaging probe 300, and the first interlocking feature and the second interlocking feature are configured to mate and releasably interlock the medical instrument 310 and the imaging probe 300 in a predetermined arrangement. In some instances, the interlocking features enable efficient and accurate alignment of the imaging probe 300 within the working channel 320 and, in some instances, to limit the rotation of the imaging probe 300 within the working channel 320. FIGS. 10 and 11 illustrate two additional examples of interlocking features.

FIG. 10 illustrates an exemplary distal probe tip 700 including an interlocking feature 705. The distal probe tip 700 may be the same as the distal tip 500 shown in FIG. 5 except for the addition of the interlocking feature 705. In the pictured embodiment, the interlocking feature 705 comprises a hemi-cylindrical protrusion disposed on an outer surface 708 of the distal probe tip 700. The interlocking feature 705 may comprise a length of metal wire, polymeric rod, glass fiber, or other suitable rigid or semi-rigid member. The interlocking feature may be semi-cylindrical in shape as shown in the pictured embodiment or may include any of a variety of other shapes, including, without limitation, elongated flat or curved surfaces. In the pictured embodiment, the interlocking feature 705 extends along at least a portion of the length of the distal probe tip 700. In other embodiments, the interlocking feature 705 may extend along a portion of a shaft (e.g., the shaft 608 shown in FIGS. 8 and 9) of the imaging probe. The interlocking feature 705 may be integrally formed with the distal probe tip 700 or may be affixed to the distal probe tip 700 with adhesive and/or other mechanical coupling. The interlocking feature 705 is configured to mate with a corresponding interlocking feature 710 (not shown) on the inner surface 510 of the working channel 320 (shown in FIG. 6, for example) to properly align the probe with the medical instrument 310 and, in some instances, to limit the twisting of the distal probe tip 700 relative to the medical instrument 310 (at least at the location of the interlocking feature 705). For example, the interlocking feature 710 may comprise an indentation or channel within the inner surface 510 of the working channel 320 having a complementary concave, semi-cylindrical contour to the interlocking feature 705.

FIG. 11 illustrates a perspective, cutaway view of an exemplary catheter body 800 including an interlocking feature 805. The catheter body 800 may be the same as the catheter body 315 shown in FIG. 4 except for the addition of the interlocking feature 805. In the pictured embodiment, the interlocking feature 805 comprises a circumferential collar of indentations or slots 805 having trapezoidal shapes. The interlocking feature 805 is disposed on an inner surface 808 of a working channel 810 of the catheter body 800. The inner surface 808 may correspond to the inner surface 510 of the working channel 320 (shown in FIG. 6, for example). The interlocking feature 805 may comprise any number and arrangement of slots or indentations having any of a variety of shapes or outlines such as, by way of non-limiting example, curves, waves, crescents, or polygonal. In the pictured embodiment, the interlocking feature 805 is disposed at a distal portion 810 of the working channel 810, adjacent a distal end 815 of the catheter body 800. In other embodiments, the interlocking feature 805 may be disposed at a more proximal portion of the catheter body 800. The interlocking feature 805 is configured to mate with a corresponding interlocking feature 820 (not shown) on an outer surface of an imaging probe (the outer surface 708 of the distal probe tip 700 shown in FIG. 10, for example) to properly align the imaging probe and the catheter body 800 and, in some instances, to limit the twisting of the distal probe tip relative to the catheter body 800 (at least at the location of the interlocking feature 805). For example, the interlocking feature 820 may comprise a protrusion or collar of protrusions on the outer surface of the imaging probe, and the protrusions may have a complementary shape or profile to the shape or profile of the interlocking feature 805. In some instances, a collared or circumferential interlocking feature having a repeating pattern, such as the interlocking feature 820, allows the user to more efficiently and easily interlock the imaging probe and the catheter because less rotation is necessary to find the interlocking feature or keying feature.

Figure 16:
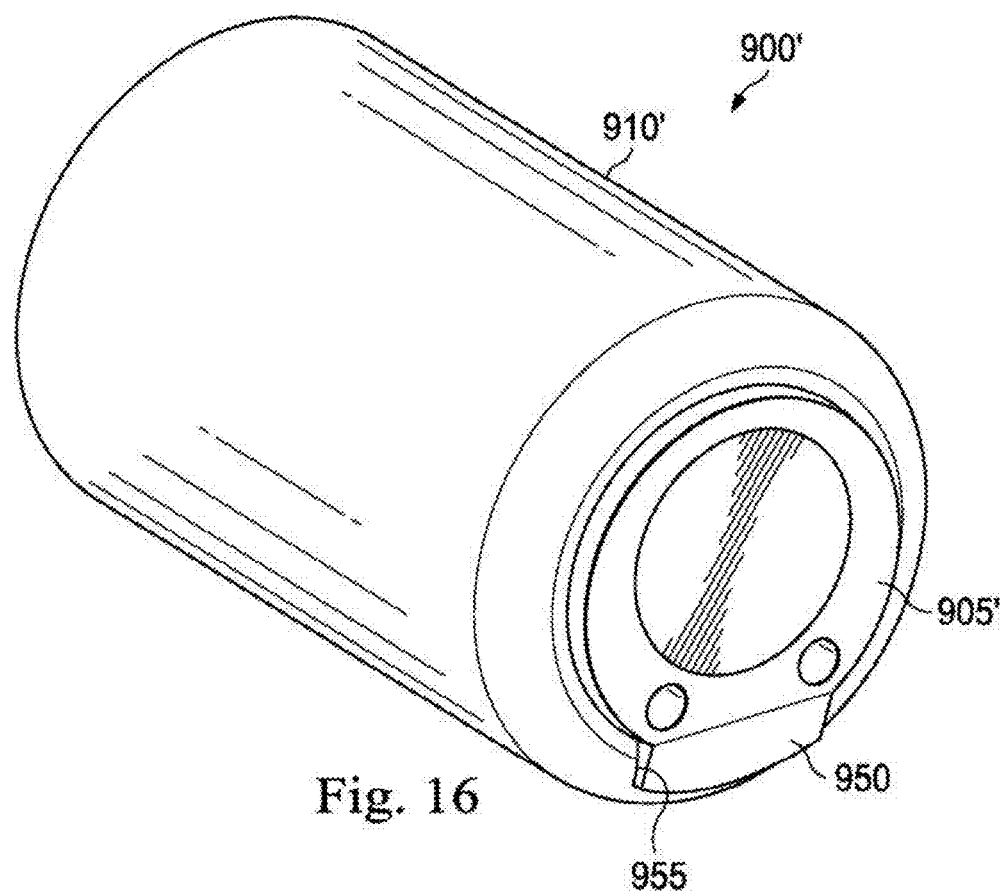
FIG. 16 is a perspective view of an exemplary medical instrument system including an exemplary imaging probe positioned within an exemplary medical instrument and exemplary interlocking features according to one embodiment of the present disclosure.
Figure 17:
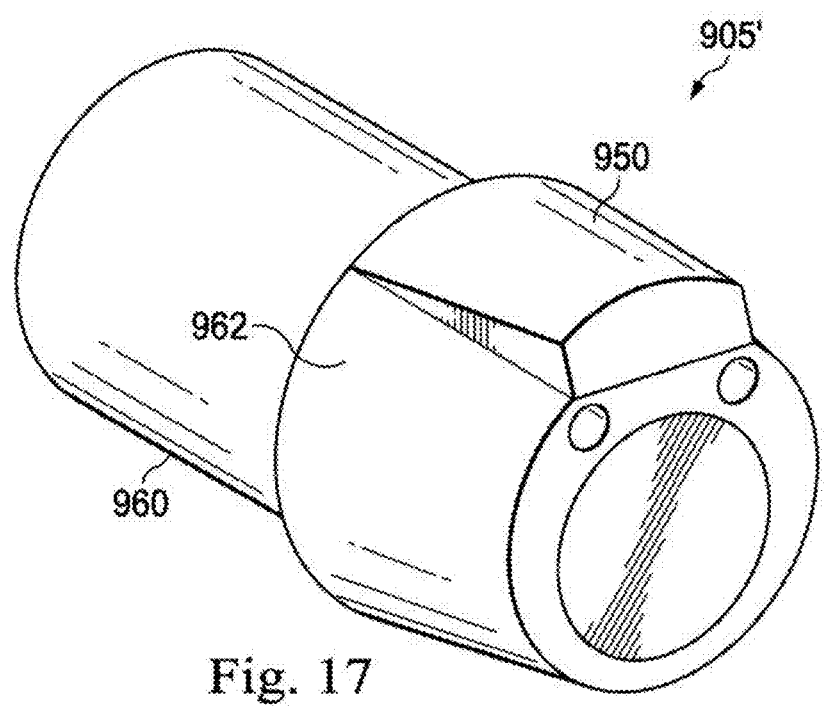
FIG. 17 is a perspective view of an exemplary distal portion of the imaging probe shown in FIG. 16 according to one embodiment of the present disclosure.
Figure 18:
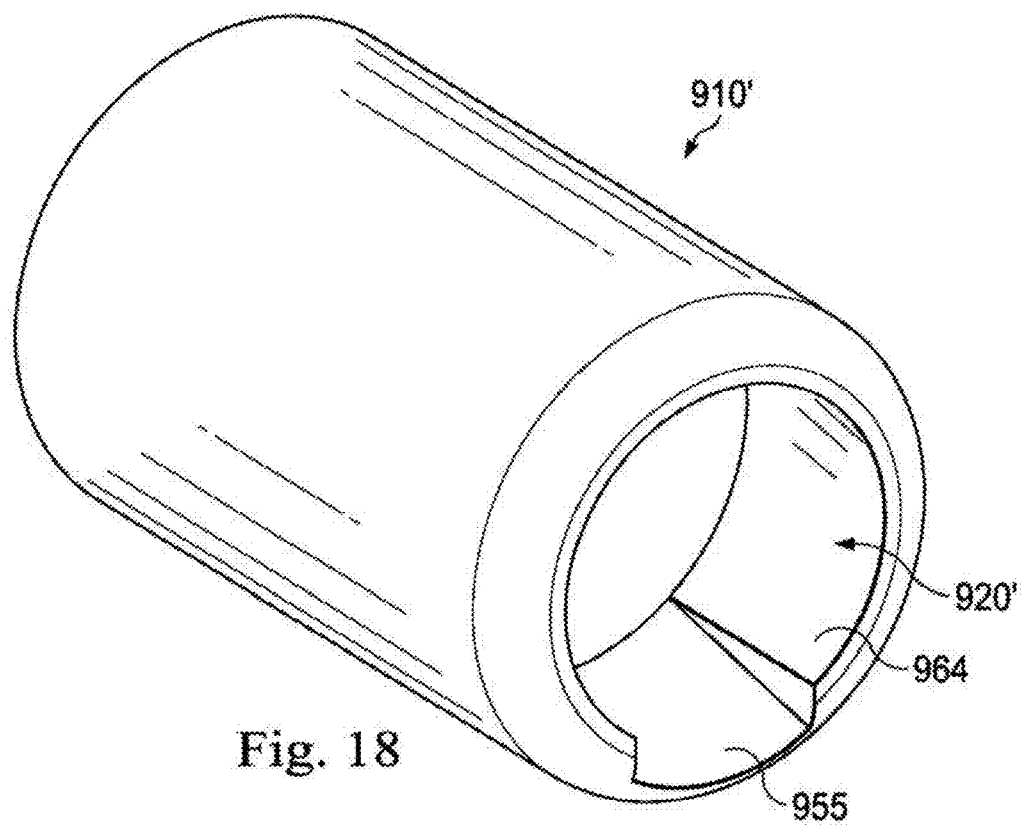
FIG. 18 is a perspective view of an exemplary distal portion of the medical instrument shown in FIG. 16 according to one embodiment of the present disclosure.

In some embodiments, the interlocking features, such as, by way of non-limiting example, the interlocking features 705, 710 discussed in relation to FIG. 10 and the interlocking features 805, 820 discussed in relation to FIG. 11, prevent or minimize liquid from pooling between the working channel 320 and the imaging probe 300. In some instances, if the user employs a proximal clamp-like device on the shaft of the imaging probe with a Touhy valve, friction can prevent the imaging probe 300 from rotating with respect to the working channel 320, which may allow for rotational referencing of the image with respect to models and 3D space. If friction is not sufficient to prevent rotation of the imaging tool 300 with respect to the working channel 320, the interlocking features may be configured to provide keying functions in addition to interlocking functions (e.g., as shown in FIGS. 16-18).

Figure 12:
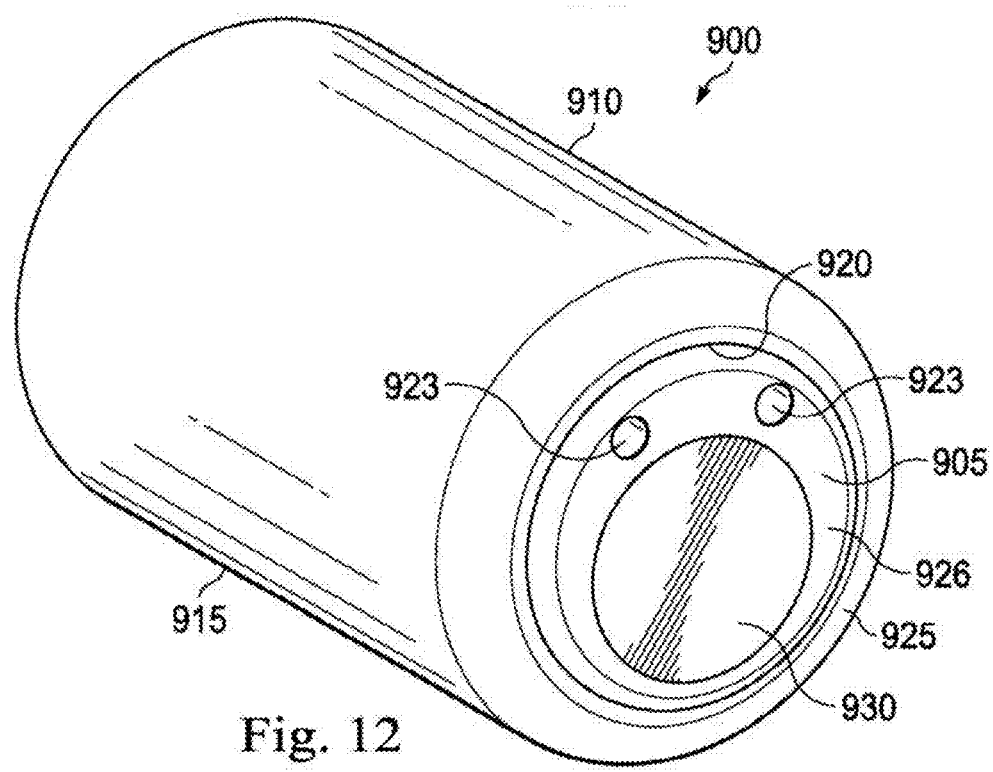
FIG. 12 is a perspective view of an exemplary medical instrument system including an exemplary imaging probe positioned within an exemplary medical instrument according to one embodiment of the present disclosure.
Figure 13:
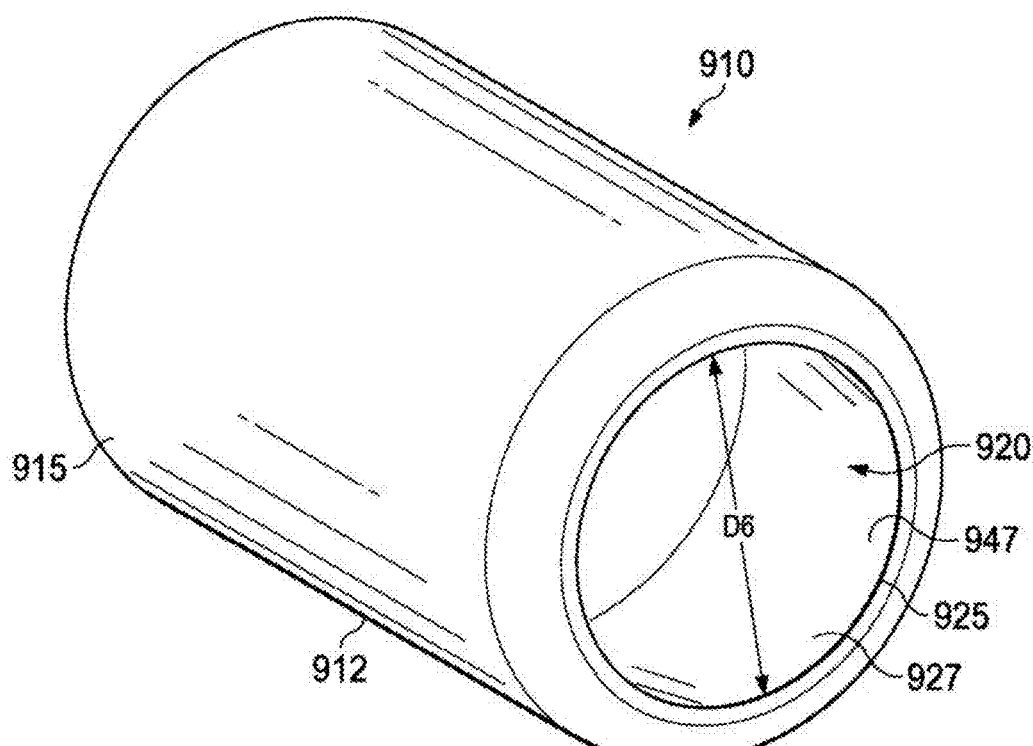
FIG. 13 is a perspective view of an exemplary distal portion of the medical instrument shown in FIG. 12 according to one embodiment of the present disclosure.
Figure 14:
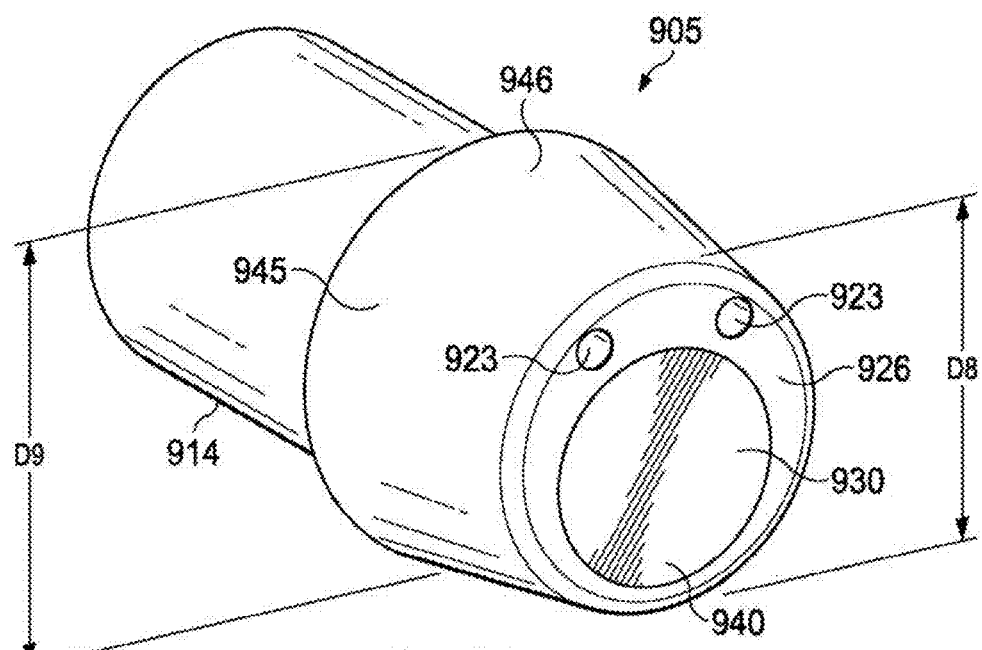
FIG. 14 is a perspective view of an exemplary distal portion of the imaging probe shown in FIG. 12 according to one embodiment of the present disclosure.
Figure 15:
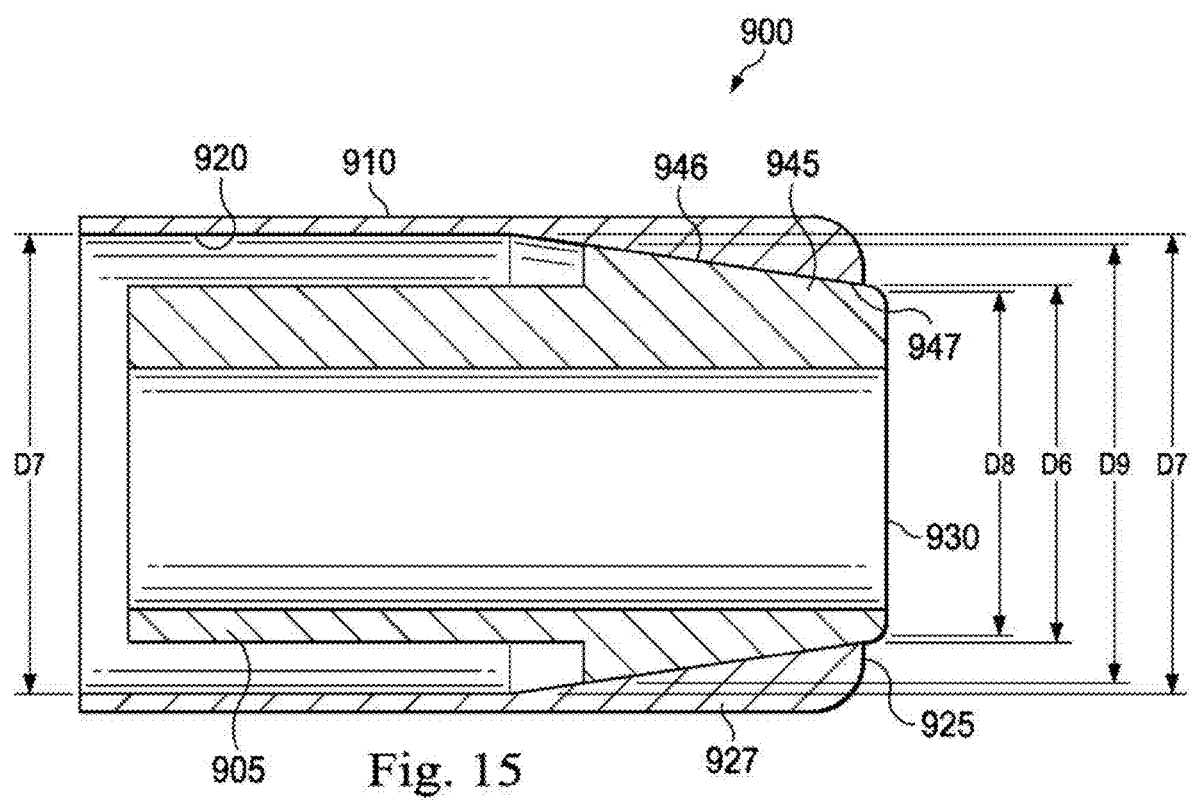
FIG. 15 is a cutaway side view of the imaging probe positioned within the medical instrument of the medical instrument system shown in FIG. 12 according to one embodiment of the present disclosure.

FIGS. 12-15 illustrate different component parts and perspectives of an exemplary medical instrument system 900 that is not configured to deliver cleaning fluid in the manner described above with reference to the medical instrument system 305 shown in FIG. 3B. FIG. 12 is a perspective view of the exemplary medical instrument system 900 including an exemplary imaging probe 905 positioned within an exemplary medical instrument 910 according to one embodiment of the present disclosure. FIG. 13 is a perspective view of a distal portion 912 of the medical instrument 910 shown in FIG. 12 according to one embodiment of the present disclosure. FIG. 14 is a perspective view of a distal portion 914 of the imaging probe 905 shown in FIG. 12 according to one embodiment of the present disclosure. FIG. 15 is a cutaway side view of the imaging probe 905 positioned within the medical instrument 910 according to one embodiment of the present disclosure. The medical instrument 910 is substantially similar to the medical instrument 310 described above except for the differences described herein. Similarly, the imaging probe 905 is substantially similar to the imaging probe 300 described above except for the differences described herein. In particular, the medical instrument 910 and the imaging probe 905 are shaped and size to have mating tapered distal portions configured to prevent fluid from pooling between the medical instrument 910 and the imaging probe 905 (e.g., and thus prevent pooled fluid from recontaminating the imaging probe 905). The tapered profiles of the distal portions of the medical instrument 910 and the imaging probe 905 are sealing features shaped and configured to selectively seal the space between the medical instrument 910 and the imaging probe 905. Additionally, a low positive pressure may be applied to the working channel between the catheter and imaging probe to further prevent the inflow of fluid from the patient anatomy.

The medical instrument 910 may be the same as the catheter system 202 shown in FIG. 2. In some instances, the medical instrument 910 is a flexible, elongated catheter. In other embodiments, the medical instrument 910 may comprise any of a variety of elongated medical instruments, including, without limitation, an endoscope, a bronchoscope, a flexible catheter, and a rigid delivery instrument. According to the present example shown in FIGS. 12 and 13, the medical instrument 910 comprises a catheter body 915 including a working channel 920 through which the elongated imaging probe 905 extends. In some embodiments, the at least a portion of the catheter body (e.g., a distal portion) is formed of radiopaque material, which may assist the user to visualize and guide the navigation of the medical instrument 910 through the patient's body.

In the pictured embodiment, the working channel 920 comprises a hollow, tubular space formed within the catheter body 915 of the instrument 910. In the pictured embodiment in FIG. 13, the working channel 920 includes a tapered distal section 927 (i.e., having a tapered inner diameter) that terminates at the distal end 925 of the catheter body 915. The working channel 920 includes a distal inner diameter D6 at a distal end 925 of the catheter body 915. In one embodiment, the distal inner diameter D6 measures approximately 1.8 mm. Other distal inner diameters D6 may be larger or smaller. For example, inner diameters of 1.5 mm and 2.0 mm may be suitable. As shown in best in FIG. 15, the inner diameter of the tapered distal section 927 decreases from a proximal inner diameter D7 to the distal inner diameter D6. In one embodiment, the distal inner diameter D7 measures approximately 2.4 mm. Other distal inner diameters D7 may be larger or smaller. For example, inner diameters of 2.0 mm or 2.5 mm may be suitable.

In some embodiments, the medical instrument system 900 includes a keying feature (as described below with reference to FIGS. 16-18) shaped and configured to selectively mate or releasably interlock the imaging probe 905 and the medical instrument 910.

In the pictured embodiment, the imaging probe 905 includes two separate illumination elements 923. The illumination elements 923 may comprise illumination fibers configured to illuminate the patient tissue past a distal end 926 of the imaging probe 905 (e.g., being imaged by the imaging probe 905). Although the pictured embodiment includes 2 illumination elements 923, other embodiments may include any number of illumination elements or may lack illumination elements altogether.

The imaging probe 905 includes an imaging surface or lens 930. In various embodiments, the lens 930 may comprise a substantially flat imaging surface or a curved imaging surface. In various embodiments, the lens 930 may be substantially co-planar with the distal end 926 of the imaging probe 905 or slightly raised from the distal end 926 of the imaging probe 905. For example, in some embodiments, the lens 930 can protrude distally past the remainder of the distal end 926 of the imaging probe 905. These configurations allow a user to wipe of the lens 930 against patient tissue to clear the lens 330 of debris. As mentioned above in relation to the lens 330, in some instances, the lens 930 may be coated with a hydrophobic coating 940, as shown in FIG. 14. Removing obstructions from the surface of the lens 930 may be made more efficient by applying a hydrophobic coating 940 to the surface of the lens 930 to repel liquid from the lens 930.

As shown in FIGS. 12, 14, and 15, the imaging probe 905 is shaped and configured to be slidably received within the working channel 920 of the medical instrument 910. In the pictured embodiment, the shape and distal inner diameter D6 of the working channel 920 is shaped and sized to halt the distal progression of the distal end 926 of the imaging probe 905 past the distal end 925 of the catheter body 915. Thus, in the pictured embodiment, the distal end 926 of the imaging probe 905 does not extend beyond the distal end 925 of the catheter body 915. This configuration minimizes damage to patient tissues and allowing the user to wipe off accumulated fluid and other debris from the lens 930 by, for example, wiping the end of the medical instrument 910 against the patient's tissues. In other embodiments, as mentioned above, a portion of the lens 930 of the imaging probe 905 may extend past the distal end 925 of the catheter body 915.

In the pictured embodiment in FIGS. 14 and 15, the imaging probe 905 includes a tapered distal section 945 (i.e., having a tapered outer diameter) that terminates at the distal end 926 of the imaging probe 905. The imaging probe 905 includes a distal outer diameter D8 at a distal end 925 of the imaging probe 905. In one embodiment, the distal outer diameter D8 measures approximately 1.8 mm. Other distal outer diameters D8 may be larger or smaller. For example, outer diameters of 1.5 mm or 2.0 mm may be suitable. In some embodiments, the distal outer diameter D8 is slightly smaller than the distal inner diameter D6 of the working channel 920. As shown in best in FIG. 15, the outer diameter of the tapered distal section 945 decreases from a proximal outer diameter D9 to the distal outer diameter D8. In one embodiment, the distal outer diameter D9 measures approximately 2.4 mm. Other distal inner diameters D9 may be larger or smaller. For example, an inner diameter of 2.0 mm or 2.5 mm may be suitable.

The tapered distal section 945 is configured to contact the tapered distal section 927 of the working channel 920. The tapered distal section 945 and the tapered distal section 927 comprise sealing features shaped and configured to prevent the passage of fluid between the working channel 920 and the imaging probe 905. In the pictured embodiment, the shape and size of the tapered distal section 945 of the imaging probe 905 is configured to substantially "match" and mate with the tapered distal section 927 of the working channel 920, thereby permitting the distal section 945 of the imaging probe 905 to be received snugly within the distal section 927 of the working channel 920 with an outer surface 946 of the imaging probe 905 in contact with an inner surface 947 of the working channel 920. Thus, in some embodiments, the distal outer diameter D8 is slightly smaller than the distal inner diameter D6 of the working channel 920, and the proximal outer diameter D9 is slightly smaller than the proximal inner diameter D7 of the working channel 920.

In some embodiments, as described above with respect to the medical instrument system 305, the medical instrument system 900 includes at least one interlocking feature shaped and configured to selectively mate or releasably interlock the imaging probe 905 and the medical instrument 910 to enable efficient and accurate alignment of the imaging probe 905 within the working channel 920 and, in some instances, to limit the rotation of the imaging probe 905 within the working channel 920. FIG. 16 illustrates an exemplary medical instrument system 900' including interlocking features 950, 955 configured to selectively mate and releasably interlock an imaging probe 905' and a medical instrument 910'. The medical instrument system 900' is substantially similar to the medical instrument system 900 described above with reference to FIGS. 12-15 except for the addition of interlocking features 950, 955, as described herein. As shown in FIG. 16, the interlocking features 950, 955 have complementary shapes and sizes configured to mate (e.g., fit together like puzzle pieces) and releasably interlock the imaging probe 905' and the medical instrument 910'.

FIG. 17 illustrates an exemplary distal probe tip 960 of the imaging probe 905' including the interlocking feature 950. The imaging probe 905' may be the same as the imaging probe 905 shown in FIG. 14 except for the addition of the interlocking feature 950. Thus, the distal probe tip 960 has a tapered shape corresponding to the tapered shape of the medical instrument 910'. In the pictured embodiment, the interlocking feature 950 comprises a wedge-shaped protrusion disposed on an outer surface 962 of the distal probe tip 950. The interlocking feature 950 may comprise a length of metal wire, polymeric rod, glass fiber, or other suitable rigid or semi-rigid member. The interlocking feature may be wedge-like in shape as shown in the pictured embodiment or may include any of a variety of other shapes, including, without limitation, elongated flat or curved surfaces. In the pictured embodiment, the interlocking feature 950 extends along at least a portion of the length of the distal probe tip 950. In other embodiments, the interlocking feature 950 may extend along a portion of a shaft (e.g., similar to the shaft 608 shown in FIGS. 8 and 9) of the imaging probe 905'. The interlocking feature 950 may be integrally formed with the distal probe tip 950 or may be affixed to the distal probe tip 950 with adhesive and/or other mechanical coupling.

Figure 19:
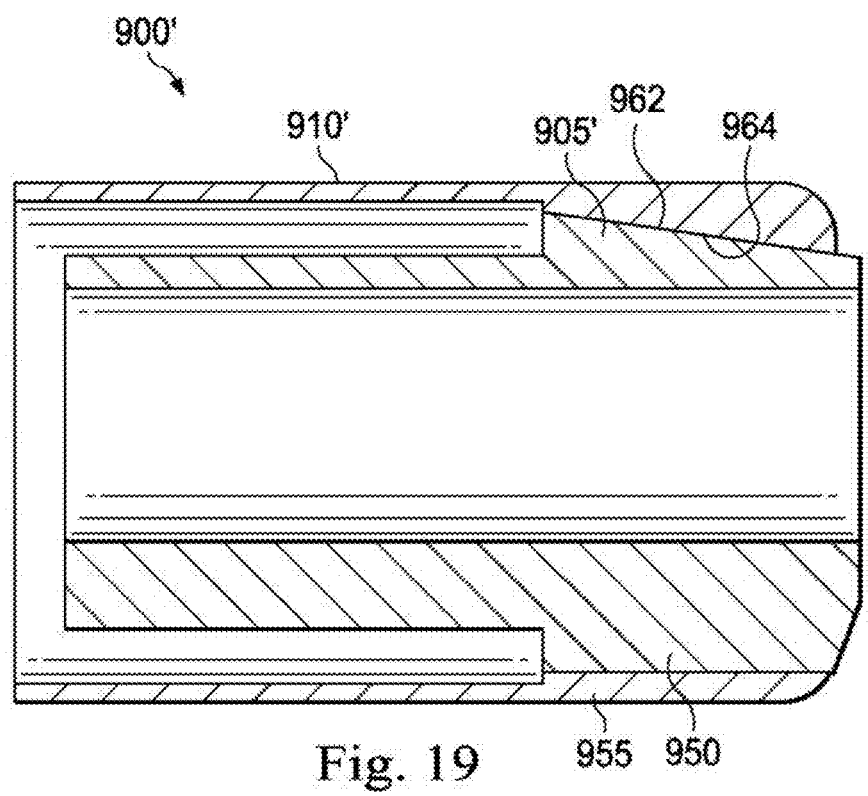
FIG. 19 is a cutaway side view of the imaging probe positioned within the medical instrument of the medical instrument system shown in FIG. 16 according to one embodiment of the present disclosure.

FIG. 18 illustrates a perspective view of the medical instrument 910' including an interlocking feature 955. The medical instrument 910' may be the same as the medical instrument 910 shown in FIG. 13 except for the addition of the interlocking feature 955. FIG. 19 illustrates a cutaway side view of the medical instrument system 900' according to one embodiment of the present disclosure. As shown best in FIGS. 16 and 19, the interlocking feature 950 is configured to mate with the corresponding interlocking feature 955, which is disposed on an inner surface 964 of a working channel 920' to properly align the probe 905' with the medical instrument 910' and, in some instances, to limit the twisting of the distal probe tip 950 relative to the medical instrument 910' (at least at the location of the interlocking feature 950). In the pictured embodiment, the interlocking feature 955 comprises an indentation within the inner surface 964 of the working channel 920' having a concave, wedge-shaped contour that is complementary to the contour of the interlocking feature 950.

The interlocking features 950, 955 may comprise any number and arrangement of protrusion or indentations having any of a variety of shapes or outlines such as, by way of non-limiting example, curves, waves, crescents, or polygons. In the pictured embodiment, the interlocking features 950, 955 are disposed at distal portions of the medical instrument system 900. In other embodiments, the interlocking features 950, 955 may be disposed at more proximal portions of the medical instrument system 900. In some embodiments, the interlocking features 950, 955 prevent or minimize liquid from pooling between the working channel 920' and the imaging probe 905'. The interlocking features 950,955 are also configured to provide keying functionality to the medical instrument system 900.

The devices, systems, and methods of this disclosure may be used for connected bronchial passageways of the lung. The devices, systems, and methods may also be suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control processing system 600. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical instrument system, comprising:
    an imaging probe including a distal tip terminating at a first distal end of the imaging probe, the distal tip including a first sealing feature and a fluid direction surface, wherein the first sealing feature extends circumferentially around the distal tip and between a radially outer surface of the imaging probe and a distal face of the distal tip of the imaging probe; and
    an elongated medical instrument having a distal portion terminating at a second distal end, the elongated medical instrument including a working channel and a second sealing feature on a surface of the working channel;
    wherein the first sealing feature and the second sealing feature are complementarily shaped such that the second sealing feature is configured to receive the first sealing feature, and wherein the first sealing feature and the second sealing feature are configured to contact one another to prevent a passage of fluid between the first and second sealing features; and
    wherein when the first and second sealing features are in contact, a gap is formed between the fluid direction surface and the second distal end of the elongated medical instrument to direct passage of fluid from the working channel across the distal tip of the imaging probe.

2. The medical instrument system of claim 1, wherein the first sealing feature comprises an external bevel at the first distal end of the imaging probe, and the second sealing feature comprises a chamfered surface of the working channel at the second distal end of the elongated medical instrument.

3. The medical instrument system of claim 2, wherein the chamfered surface is a 360° circumferential surface and the external bevel has a first circumferential end and a second circumferential end and wherein the fluid direction surface extends between the first and second circumferential ends.

4. The medical instrument system of claim 1 wherein the fluid direction surface is sloped between an outer circumferential surface of the imaging probe and a surface of the first distal end of the imaging probe.

5. The medical instrument system of claim 4 wherein the fluid direction surface comprises at least one of a curved slope, a flat slope, and a slope of approximately 60°.

6. The medical instrument system of claim 1 wherein the gap has a dimension of approximately 0.002 inches.

7. The medical instrument system of claim 1, wherein the first and second sealing features are shaped and configured to mate and prevent the first distal end of the imaging probe from extending past the second distal end of the second distal end of the working channel.

8. The medical instrument system of claim 1, further including:
    a first interlocking feature disposed on the imaging probe; and
    a second interlocking feature disposed on the working channel of the elongated medical instrument; and
    wherein the first interlocking feature and the second interlocking feature are configured to mate and releasably interlock the imaging probe in a predetermined arrangement relative to the elongated medical instrument.

9. The medical instrument system of claim 8, wherein the first and second interlocking features are configured to limit rotation of the imaging probe within the working channel.

10. The medical instrument system of claim 8, wherein one of the first and second interlocking features includes a protrusion and the other of the first and second interlocking features includes a recess shaped to complement and receive the protrusion.

11. The medical instrument system of claim 8, wherein the first interlocking feature comprises a first collar including a plurality of protrusions on an external surface of the imaging probe, the first collar having a first three-dimensional shape, and wherein the second interlocking feature comprises a second collar including a plurality of indentations on an internal surface of the working channel, the second collar having a second three-dimensional shape complementary to the first three-dimensional shape.

12. The medical instrument system of claim 1, further including a lens disposed on the imaging probe.

13. The medical instrument system of claim 12, wherein the distal tip of the imaging probe comprises an optically clear distal tip encasing the lens.

14. The medical instrument system of claim 12, wherein the lens is coated with a hydrophobic coating.

15. The medical instrument system of claim 1 further comprising a fluid management system for maintaining a positive pressure in the working channel to limit ingress of fluid from an area external to the elongated medical instrument.

16. A method, comprising:
positioning an imaging probe within a working channel of an elongate medical instrument, wherein the imaging probe includes a distal tip having a first shape and the working channel includes a distal portion having a second shape, the first shape and the second shape being complementary;
selectively interlocking the imaging probe and the elongated medical instrument by aligning a first interlocking feature disposed on an external surface of the imaging probe with a second interlocking feature disposed on an internal surface of the working channel; and
selectively sealing a fluid passage between the imaging probe and the elongated medical instrument by advancing the distal tip of the imaging probe within a distal portion of the elongated medical instrument.

17. The method of claim 16, wherein selectively sealing a fluid passage between the imaging probe and the elongated medical instrument comprises aligning a first sealing feature disposed on an external surface of the imaging probe with a second sealing feature disposed on an internal surface of the working channel.

18. The method of claim 17, wherein the first sealing feature and the second sealing feature include complementary three-dimensional shapes configured to contact one another.

19. The method of claim 16, further comprising directing fluid from the working channel across a sloped nozzle portion on the distal tip of the imaging probe and across a distal end of the imaging probe.

20. The method of claim 19, wherein the distal end of the imaging probe comprises a lens.

21. The method of claim 19, wherein the distal tip of the imaging probe comprises a clear distal tip encasing a lens, and the distal end of the imaging probe comprises a surface of the clear distal tip.

22. A medical instrument system, comprising:
an imaging probe including a distal tip terminating at a first distal end of the imaging probe, the distal tip including a first sealing feature having a first shape and a fluid direction surface;
an elongated medical instrument having a distal portion terminating at a second distal end, the elongated medical instrument including a working channel and a second sealing feature having a second shape on a surface of the working channel;
a first interlocking feature disposed on an external surface of the imaging probe; and
a second interlocking feature disposed on an internal surface of the working channel, wherein the imaging probe is configured to be selectively interlocked with the elongated medical instrument by aligning the first interlocking feature with the second interlocking feature when the imaging probe is positioned within the working channel of the elongated medical instrument;
wherein the first shape and the second shape are complementary, and wherein the first sealing feature and the second sealing feature are shaped and configured to contact one another to prevent passage of fluid between the first and second sealing features when the distal tip of the imaging probe has been advanced within the distal portion of the elongated medical instrument; and
wherein when the first and second sealing features are in contact, a gap is formed between the fluid direction surface and the second distal end of the elongated medical instrument to direct passage of fluid from the working channel across the distal tip of the imaging probe.

23. The medical instrument system of claim 22, wherein the first sealing feature comprises a first interlocking sealing feature, wherein the second sealing feature comprises a second interlocking sealing feature, and wherein the first interlocking sealing feature is configured to be selectively interlocked with the second interlocking sealing feature.

24. The medical instrument system of claim 22, wherein each of the first interlocking feature and the second interlocking feature includes at least one of a projection or an indentation, and wherein the first interlocking feature and the second interlocking feature are configured to cooperate to position the imaging probe along a central axis of the working channel.

* * * * *